United States Patent
Goebel et al.

(10) Patent No.: US 11,769,596 B2
(45) Date of Patent: Sep. 26, 2023

(54) PLASMA BASED PROTEIN PROFILING FOR EARLY STAGE LUNG CANCER DIAGNOSIS

(71) Applicant: Lung Cancer Proteomics, LLC, Michigan City, IN (US)

(72) Inventors: Cherylle Goebel, Mountain View, CA (US); Christopher Louden, Bandera, TX (US); Thomas C Long, Valparaiso, IN (US)

(73) Assignee: LUNG CANCER PROTEOMICS LLC, Valparaiso, IN (US)

( * ) Notice: Subject to any disclaimer, the term of this patent is extended or adjusted under 35 U.S.C. 154(b) by 0 days.

(21) Appl. No.: 16/209,683

(22) Filed: Dec. 4, 2018

(65) Prior Publication Data

US 2019/0221316 A1    Jul. 18, 2019

Related U.S. Application Data

(63) Continuation of application No. PCT/US2018/026119, filed on Apr. 4, 2018.

(60) Provisional application No. 62/481,474, filed on Apr. 4, 2017.

(51) Int. Cl.

| | |
|---|---|
| *G16H 50/50* | (2018.01) |
| *G16H 50/20* | (2018.01) |
| *G16H 50/70* | (2018.01) |
| *G16B 40/00* | (2019.01) |
| *G06N 3/042* | (2023.01) |
| *G16H 50/30* | (2018.01) |
| *G06N 20/10* | (2019.01) |
| *G16B 5/00* | (2019.01) |
| *G06F 17/15* | (2006.01) |
| *G06F 17/18* | (2006.01) |
| *G06N 3/086* | (2023.01) |
| *G16H 10/40* | (2018.01) |
| *G16B 20/00* | (2019.01) |
| *C12Q 1/6806* | (2018.01) |
| *C12Q 1/6825* | (2018.01) |
| *C12Q 1/6827* | (2018.01) |
| *C12Q 1/6886* | (2018.01) |

(52) U.S. Cl.
CPC .......... *G16H 50/50* (2018.01); *C12Q 1/6806* (2013.01); *C12Q 1/6825* (2013.01); *C12Q 1/6827* (2013.01); *C12Q 1/6886* (2013.01); *G06F 17/15* (2013.01); *G06F 17/18* (2013.01); *G06N 3/042* (2023.01); *G06N 3/086* (2013.01); *G06N 20/10* (2019.01); *G16B 5/00* (2019.02); *G16B 40/00* (2019.02); *G16H 50/20* (2018.01); *G16H 50/30* (2018.01); *G16H 50/70* (2018.01); *G16B 20/00* (2019.02); *G16H 10/40* (2018.01)

(58) Field of Classification Search
None
See application file for complete search history.

(56) References Cited

U.S. PATENT DOCUMENTS

| | | |
|---|---|---|
| 6,939,670 B2 | 9/2005 | Pressman et al. |
| 7,288,249 B2 | 10/2007 | Carter et al. |
| 7,612,181 B2 | 11/2009 | Wu et al. |
| 7,624,076 B2 | 11/2009 | Movellan et al. |
| 7,845,050 B2 | 12/2010 | Pyo |
| 7,888,051 B2 | 2/2011 | Streeper et al. |
| 8,541,183 B2 | 9/2013 | Streeper et al. |
| 8,771,963 B2 | 7/2014 | Nakamura et al. |
| 9,852,269 B2 | 12/2017 | Sakagawa et al. |
| 9,952,220 B2 | 4/2018 | Michalek et al. |
| 10,359,425 B2 | 7/2019 | Gold et al. |
| 2003/0104499 A1 | 6/2003 | Pressman et al. |
| 2003/0134339 A1 | 7/2003 | Brown |
| 2003/0190602 A1 | 10/2003 | Pressman et al. |
| 2006/0024692 A1 | 2/2006 | Nakamura et al. |
| 2006/0084126 A1 | 4/2006 | Segal |
| 2006/0088894 A1 | 4/2006 | Wright et al. |
| 2006/0252057 A1 | 11/2006 | Raponi et al. |
| 2007/0092917 A1 | 4/2007 | Guyon |
| 2008/0109389 A1 | 5/2008 | Polyak et al. |
| 2008/0133141 A1 | 6/2008 | Frost |
| 2009/0069189 A1 | 3/2009 | Streeper et al. |
| 2010/0009386 A1 | 1/2010 | Streeper et al. |
| 2010/0070191 A1* | 3/2010 | Gold ............... G01N 33/57423 702/19 |
| 2012/0021946 A1 | 1/2012 | Nakamura et al. |

(Continued)

FOREIGN PATENT DOCUMENTS

| | | |
|---|---|---|
| CN | 1346279 | 4/2002 |
| CN | 2002542485 | 12/2002 |

(Continued)

OTHER PUBLICATIONS

Dass et al. (Intl. Conf. on Control, Instrum., Energy & Comm. (CIEC) IEEE pp. 558-562), (Year: 2014).*
Lee et al. (General Thoracic Surgery vol. 143:421-427) (Year: 2012).*
Ma et al. (Oncotarget vol. 8:18901-18913; published Jan. 21, 2017). (Year: 2017).*
Boeri et al. (2011) PNAS, vol. 108, No. 9, pp. 3717-3718.
Bosse et al., Am J Respir and Crit Care Med, 1999, vol. 159, pp. 596-602.
Camilla et al., Clin Diag Lab Immun, 2001, vol. 8, pp. 776-784.
Chiu et al., Am J Resp Cell Mol Bio, 2003, vol. 29, pp. 106-116.
Chung et al., Thorx, 1999, Vol. 54, pp. 825-857.
Cohen et al., Am J Phys, 2006, vol. 290, No. 6, pp. L1097-L1103.
Dai et al., Sci Chin Series C: Life Sci, 2007, vol. 50, No. 3, pp. 305-311.

(Continued)

*Primary Examiner* — Lori A. Clow
(74) *Attorney, Agent, or Firm* — ArentFox Schiff LLP

(57) ABSTRACT

The invention provides biomarkers and combinations of biomarkers useful in diagnosing non-small cell lung cancer. Measurements of these biomarkers are inputted into a classification system such as Random Forest to assist in determining the likelihood that an individual has non-small cell lung cancer. Kits comprising agents for detecting the biomarkers and combination of biomarkers, as well as systems that assist in diagnosing non-small cell lung cancer are also provided.

10 Claims, 1 Drawing Sheet

(56) References Cited

U.S. PATENT DOCUMENTS

| | | |
|---|---|---|
| 2015/0031561 A1 | 1/2015 | Bertenshaw et al. |
| 2017/0073763 A1 | 3/2017 | Diehn et al. |

FOREIGN PATENT DOCUMENTS

| | | | | |
|---|---|---|---|---|
| CN | 1621829 | | 6/2005 | |
| CN | 1705753 | | 7/2005 | |
| CN | 1977052 | | 6/2007 | |
| CN | 101346626 | | 1/2009 | |
| CN | 101587125 | | 11/2009 | |
| CN | 101978269 | | 2/2011 | |
| CN | 101988059 | | 3/2011 | |
| CN | 102037355 | | 4/2011 | |
| CN | 103703371 | A | 4/2014 | |
| CN | 105005680 | A | 10/2015 | |
| CN | 110444287 | A | 11/2019 | |
| JP | 2004526154 | | 8/2004 | |
| JP | 2006509186 | | 3/2006 | |
| JP | 2009501318 | | 1/2009 | |
| JP | 2009524008 | | 6/2009 | |
| JP | 2010523979 | | 7/2010 | |
| JP | 2011506917 | | 3/2011 | |
| WO | 1998035985 | | 8/1998 | |
| WO | 2000063698 | | 10/2000 | |
| WO | 2002073204 | | 9/2002 | |
| WO | 2003087840 | | 10/2003 | |
| WO | 2003101283 | A2 | 12/2003 | |
| WO | 2004030511 | | 4/2004 | |
| WO | 2004031413 | | 4/2004 | |
| WO | 2005003164 | | 1/2005 | |
| WO | 2005090603 | | 9/2005 | |
| WO | 2005098445 | | 10/2005 | |
| WO | 2006045318 | | 5/2006 | |
| WO | 2006118522 | | 11/2006 | |
| WO | 2007002677 | | 1/2007 | |
| WO | 2007013671 | | 2/2007 | |
| WO | 2007026773 | | 3/2007 | |
| WO | 2007064964 | | 6/2007 | |
| WO | 2008063413 | | 5/2008 | |
| WO | 2008106200 | | 9/2008 | |
| WO | 2008124138 | | 10/2008 | |
| WO | 2009006323 | | 1/2009 | |
| WO | 2009036123 | | 3/2009 | |
| WO | 2009074276 | | 6/2009 | |
| WO | 2010030697 | | 3/2010 | |
| WO | 2005066564 | | 5/2015 | |
| WO | WO-2015066564 | A1 * | 5/2015 | ............ G16B 20/00 |
| WO | 2015088947 | A1 | 6/2015 | |

OTHER PUBLICATIONS

Dass et al., International Conference on Control, Instrum., Energy & Commerce (CIEC) IEEE (2014) pp. 558-562.
Diaz-Urizrte et al., BMC Cioinformatics (2006) vol. 7, p. 3.
Eboshida et al., The 2007 Fiscal Year General Report and Report to Allotted Studies (2008) pp. 48-51.
Hofmann et al., Oncology Report (2006) vol. 16, pp. 587-595.
Huang et al., Can Res (Sep. 2005) vol. 55, pp. 3847-3853.
Iizasa, Clin Can Res, 1999, vol. 5, No. 1, pp. 149-153.
Izbicka et al. (2012) Cancer Genomics & Proteomics, vol. 9, pp. 27-36.
Izuhara et al., Curr Med Chem, 2006, vol. 13, pp. 2291-2298.
Kasayama et al., The Allergy in Practice, 2005, vol. 335, pp. 757-759.
Kikuchi, J Juzen Med Soc, 1998, vol. 107, No. 6, pp. 434-445.
Kips, Eur Resp J, 2001, vol. 18, Supplemental 34, pp. 24s-33s.
Koizumi et al., Clin Exp Immun, 1995, vol. 101, pp. 468-473.
Koomen et al., Rapid Comm Mass Spectrometry, 2004, vol. 18, No. 21, pp. 2537-2548.
Lee et al., General Thoracic Surgery (2012) vol. 143, pp. 421-427.
Leonardi et al., Clin Experimental Allergy, 2007, vol. 37, No. 6, pp. 872-879.
Liu et al., Clin Chem, 2005, vol. 51, No. 7. pp. 1102-1109.
Ma et al., Biochem Biophys Res Comm, 2008, vol. 371, No. 3, pp. 425-430.
Ma et al., Oncotarget (2017) vol. 8 pp. 18901-18913, published Jan. 21, 2017.
Mandrekar et al., J. Biopharm Stat, 2009, vol. 19, pp. 530-542.
Mattos et al., Chest, 2002, vol. 122, pp. 1543-1552.
Moller et al., J Hepatology, 2007, vol. 47, pp. 671-676.
Obase et al., Med Frontline, 2006, vol. 61, No. 3, pp. 85-490.
Oh et al., Proteomics, 2001, vol. 1, No. 10, pp. 1303-1319.
Oh et al., Am J Resp Cell Mol Bio, 2008, vol. 40, pp. 568-574.
Okano et al., Proteomics, 2006, vol. 6, No. 13, pp. 3938-3948.
Orditura et al., J Interferon & Cytokine Res, 2002, vol. 22, pp. 1129-1135.
Oshita et al., Oncol Rep, 2010, vol. 24, pp. 637-645.
Oyama et al., Anticancer Res, 2005, vol. 25, pp. 1193-1196.
Paik, Curr Opin Obstet Gynecol, 2006, vol. 18, pp. 59-63.
Pan et al., Lung, 2008, vol. 186, pp. 255-261.
Patnaik et al., Cancer Research, 2010, vol. 70, No. 1, pp. 36-45.
Saji et al, BIotherapy, 2002, vol. 16, No. 6, pp. 535-540.
Schapire, The Strength of Weak Learnability, Machine Learning, 1990, vol. 5, pp. 197-227.
Shi et al., ACTA Academiae Medicinenea Suzhou, 2001, vol. 21, No. 2, pp. 149-151.
Siegfried et al., Soc Thoracic Surg, 1998, vol. 66, pp. 1915-1918.
Snell et al., Curr Opin Pharm, 2008, vol. 8, pp. 222-235.
Tan et al., Ensemble machine learning on gene expression data for cancer classification, 2003, Applied BIoinformatics, vol. 2, Supplemental 3, S75-S83.
Voorzanger-Rousselot et al., Can Treatment Rev, 2007, vol. 33, No. 3, pp. 230-283.
Wagner et al., Proteomics, 2003, vol. 3, No. 9, pp. 1692-1698.
Wang, Chinese Doctoral Dissertations Full-text Database Information Science and Technology, vol. 8, pp. 1140-1224.
Wills-Karp et al., Pulm Med, 2003, vol. 9, pp. 21-27.
Wu et al., J Hygiene Res, 2000, vol. 29, No. 4, pp. 213-215.
Xia Xuewel et al., Chin J Lab Diagn., 2005, vol. 9, No. 3, pp. 424-426.
Yanagisawa et al., Lancet, 2003, vol. 362, pp. 433-439.
Yanagisawa et al., J Nat' Can Instit, 2007, vol. 99, No. 11, pp. 858-867.
Yang et al., Med. Oncol., 2008, vol. 25, No. 4, pp. 380-386.
Yeo et al., Proteomics, 2004, vol. 4, No. 11, pp. 3308-3317.
Yoshikawa et al., Jap J Rhinology, 2007, vol. 46, No. 3, pp. 237.
Zhang et al., Prac Prev Med, 2007, vol. 14, No. 3, pp. 891-893.
Zhou et al., Chin J Lab Diag., 2007, vol. 11, No. 12, pp. 1628-1631.
Han, et al., Data Mining Concepts and Techniques, Chapter 6, Classification and Prediction, 2006, pp. 285-382.

* cited by examiner

PLASMA BASED PROTEIN PROFILING FOR EARLY STAGE LUNG CANCER DIAGNOSIS

CROSS-REFERENCE TO RELATED APPLICATIONS

This application is a continuation of International Patent Application PCT/US2018/026119, filed Apr. 4, 2018, which claims priority U.S. Provisional Patent Application No. 62/481,474, filed Apr. 4, 2017, the disclosure of each of which are hereby incorporated by reference.

BACKGROUND OF THE INVENTION

Field of the Invention

The invention relates to the detection, identification, and diagnosis of lung disease using biomarkers and kits thereof, as well as systems that assist in determining the likelihood of the presence or absence of lung disease based on the biomarkers. More specifically, the invention relates to the diagnosis of non-small cell lung cancers (NSCLC) by measuring expression levels of specific biomarkers and inputting these measurements into a classification system such as Random Forest.

Description of the Related Art

Pathologies of Human Lung Tissues

The American Cancer Society, Inc. estimated 229,400 new cancer cases of the respiratory system and 164,840 deaths from cancers of the respiratory system in 2007 alone. While the five year survival rate of all cancer cases when the cancer is detected while still localized is 46%, the five year survival rate of lung cancer patients is only 13%. Correspondingly, only 16% of lung cancers are discovered before the disease has spread. Lung cancers are generally categorized as two main types based on the pathology of the cancer cells. Each type is named for the types of cells that were transformed to become cancerous. Small-cell lung cancers are derived from small cells in the human lung tissues, whereas non-small-cell lung cancers generally encompass all lung cancers that are not small-cell type. Non-small-cell lung cancers are grouped together because the treatment is generally the same for all non-small-cell types. Together, non-small-cell lung cancers (NSCLCs) make up about 75% of all lung cancers.

A major factor in the low survival rate of lung cancer patients is the fact that lung cancer is difficult to diagnose early. Current methods of diagnosing lung cancer or identifying its existence in a human are restricted to taking X-rays, Computed Tomography (CT) scans and similar tests of the lungs to physically determine the presence or absence of a tumor. The diagnosis of lung cancer is often made only in response to symptoms which have been evident or existed for a significant period of time, and after the disease has been present in the human long enough to produce a physically detectable mass.

Diagnosis of Lung Cancer

Neither sputum cytology nor chest X-rays have been found to be useful in screening for early detection of lung cancer. On the other hand, low-dose computed tomography has shown promise when applied to high risk populations (e.g., heavy smokers). Aberle et al. *N. Engl. J. Med.* (2011) 365: 395-409. However, criteria for defining at-risk populations who might benefit from this sort of screening are still not readily available, and utility of this technique for screening a more general population is less clear. While large lung nodules detected by CT scan are clearly associated with a likelihood of malignancy, the vast majority of small nodules (<7 mm) appear benign. MacMahon et al. *Radiology* (2005) 237: 395-400. Thus, supplemental screening methods to assist in early detection and diagnosis of lung cancer are needed.

Analysis of Multivariate Medical Data

In the late 1980s and early 1990s, logistic regression started being used in medicine. An example of the use of logistic regression in medicine is the Trauma Revised Injury Severity Score (TRISS). See, *Evaluating Trauma Care: The TRISS Method*. Boyd, C R, Tolson, M A and Copes, W S. 1987, Journal of Trauma, Vol. 27, pages 370-378. TRISS is used in hospitals in the United States of America as a way to predict in-hospital mortality following trauma and to make inter-hospital comparisons of trauma surgery quality. The TRISS is based on a logistic regression model of mortality following a traumatic event with injury severity score, revised trauma score and age as covariates.

Logistic regression models the logit of the probability of an event, also called the log-odds of the event, defined as $$\log\frac{p}{1-p},$$

where p is the probability of the occurrence of an event. Letting $$y = \log\frac{p}{1-p},$$

the logistic regression model can be expressed as $y=\beta'x$, where x is a vector of covariates and $\beta$ is a vector of effects for each covariate. Maximization of the likelihood function for the model yields an estimate of $\beta$. A logistic discrimination model is a logistic regression model that transforms the predicted probabilities to group labels.

The logistic regression model is based on the assumption that the effect of each covariate is linear with respect to the log-odds of the event. Harrell, Frank. *Regression Modeling Strategies*. New York: Springer, 2001, page 217. From the point of view of classification, linearity of each covariate with respect to the log-odds of the event may be sufficient to achieve a high accuracy, even in the test set; a violation of this assumption, however, could cause the model to grossly misestimate the effect and therefore result in poor performance.

A large number of events per variable (EPV) are required for stable estimates and reliable and accurate classification (*Performance of logistic regression modeling: beyond the number of events per variable, the role of data structure*. Courvoisier, D S, et al., et al. 2011, Journal of Clinical Epidemiology, Vol. 64, pp. 993-1000). The EPV needed varies as the number of variables increases and as the odds ratio (estimated by $e^\beta$) approaches unity. When the number of variables is equal to 25, for example, Courvoisier et al. (Id., p. 997) showed that, depending on the relationship between the covariates and the probability of event, EPV=25 may not be sufficient to yield adequate power and conclude that there is no single rule based on EPV that would guarantee an accurate estimation of logistic regression parameters (Id., p. 1000).

Classification Systems

Various classification systems such as machine learning approaches for data analysis and data mining have been explored for recognizing patterns and enabling the extraction of important information contained within large data bases in the presence of other information that may be nothing more than irrelevant data. Learning machines comprise algorithms that may be trained to generalize using data with known classifications. Trained learning machine algorithms may then be applied to predict the outcome in cases of unknown outcomes, i.e., to classify data according to learned patterns. Machine learning methods, which include neural networks, hidden Markov models, belief networks and kernel based classifiers such as support vector machines, are useful for problems characterized by large amounts of data, noisy patterns and the absence of general theories.

Many successful approaches to pattern classification, regression and clustering problems rely on kernels for determining the similarity of a pair of patterns. These kernels are usually defined for patterns that can be represented as a vector of real numbers. For example, the linear kernel, radial basis kernel and polynomial kernel all measure the similarity of a pair of real vectors. Such kernels are appropriate when the data can best be represented in this way, as a sequence of real numbers. The choice of kernel corresponds to the choice of representation of the data in the feature space. In many applications, the patterns have a greater degree of structure. These structures can be exploited to improve the performance of the learning algorithm. Examples of the types of structured data that commonly occur in machine learning applications are strings, documents, trees, graphs, such as websites or chemical molecules, signals, such as microarray expression profiles, spectra, images, spatio-temporal data, relational data and biochemical concentrations, amongst others.

Classification systems have been used in the medical field. For example, methods of diagnosing and predicting the occurrence of a medical condition have been proposed using various computer systems and classification systems such as support vector machines. See, e.g., U.S. Pat. Nos. 7,321,881; 7,467,119; 7,505,948; 7,617,163; 7,676,442; 7,702,598; 7,707,134; and 7,747,547. The methods described in these patents have not yet been shown to provide a consistent high level of accuracy in diagnosing and/or predicting lung disease, such as non-small lung cancer. It is desirable to develop a method to determine the existence of lung cancers early in the disease progression. It is likewise desirable to develop a method to diagnose non-small cell lung cancer, before the earliest appearance of clinically apparent symptoms.

SUMMARY OF THE PREFERRED EMBODIMENTS OF THE INVENTION

The present invention provides a classification system that uses robust methods of evaluating a set of biomarkers in a subject using various classifiers such as random forests. The inventors have developed a method of physiological characterization, based in part on a classification according to this invention, in a subject comprising first obtaining a physiological sample of the subject; then determining biomarker measures of a plurality of biomarkers in that sample; and finally classifying the sample based on the biomarker measures using a classification system, where the classification of the sample correlates to a physiologic state or condition, or changes in a disease state in the subject. Typically, the classification system includes a machine learning system, such as a classification and regression tree based classification system. The inventors' method of physiological characterization, based in part on a classification according to this invention, provides for diagnoses indicative of the presence or absence of non-small cell lung cancer in the subject, or the stage of development of non-small cell lung cancer, e.g., an early stage of development (Stage I).

The biomarker measures are typically arranged in a vector for each subject for whom the biomarker measures are obtained. In addition to the particular biomarker measures, each vector may include other information associated with the subject, including sex, age, smoking history, measures for additional biomarkers, other features of the subject's health history, and the like. The set of training vectors may comprise at least 30 vectors, at least 50 vectors, or at least 100 vectors.

In preferred modes of any embodiment(s) described herein, a human subject is considered positive for NSCLC if any of the replicate sample from the subject is classified positive by any one, any two, any three, any four, any five, any six, any seven, or any eight classifiers (up to all classifiers). In preferred modes of any embodiment(s) described herein, a subject may be considered positive if multiple replicates for a single classifier (e.g., all replicates for each classifier, two or more replicates for a single classifier, three replicates for a single classifier) or if multiple replicates across all classifiers used (e.g., two replicates across the number of classifiers used in an ensemble of classifiers, three replicates across the number of classifiers used in an ensemble of classifiers, four replicates across the number of classifiers used in an ensemble of classifiers) are classified as positive. In preferred modes of any embodiment(s) described herein, for test data sets, and for each possible total number of positives (i.e., zero to the number of classifiers multiplied by the number of replicates), the accuracy, sensitivity, specificity, and the positive and negative values were examined. In preferred modes of any embodiment(s) described herein, the number of positive replicates and/or classifier(s) required to return positive may then be determined based on the examined accuracy, sensitivity, specificity, and positive and negative values. In preferred modes of any embodiment(s) described herein, accuracy, sensitivity, specificity, positive predictive value and/or negative predictive value is above 0.7. In preferred modes of any embodiment(s) described herein, accuracy, sensitivity, specificity, positive predictive value and/or negative predictive value is above 0.8. In preferred modes of any embodiment(s) described herein at least one, more preferably two or more of, accuracy, sensitivity, positive predictive value and negative predictive value is above 0.9. In preferred modes of any embodiment(s) described herein, at least one of, more preferably two or more of, accuracy, sensitivity, specificity, positive predictive value and negative predictive value is above 0.95. In preferred modes of any embodiment(s) described herein, at least one of, more preferably two or more of, accuracy, sensitivity, specificity, positive predictive value and negative predictive value is above 0.98.

The embodiments of the present invention can be used in an enhanced method for screening a human subject to determine whether or not the human is likely to suffer from NSCLC, the enhancement comprising classifying test data from the human subject using the method according to any one of the embodiments of the invention, where the human subject is one who exhibits at least one lung nodule detectable by computerized tomography scan. An alternative use for the embodiments of the present invention provides another enhanced method for screening a human subject to determine whether or not the human is likely to suffer from NSCLC, where a human subject classified positive for NSCLC using the method of this invention is further tested for lung nodules by low-dose computerized tomography.

In one mode, this invention provides a method of classifying test data, the test data comprising a plurality of biomarker measures of each of a set of biomarkers, the method comprising: (a) receiving, on at least one processor, test data comprising a biomarker measure for each biomarker of a set of biomarkers in a physiological sample from a human test subject; (b) evaluating, using the at least one processor, the test data using a classifier which is an electronic representation of a classification system, each classifier trained using an electronically stored set of training data vectors, each training data vector representing an individual human and comprising a biomarker measure of each biomarker of the set of biomarkers for the respective human, each training data vector further comprising a classification with respect to the presence or absence of diagnosed NSCLC in the respective human; and (c) outputting, using the at least one processor, a classification of the sample from the human test subject concerning the likelihood of presence or development of NSCLC in the subject based on the evaluating step, wherein the set of biomarkers comprises at least nine (9) biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4.

In another mode, this invention provides a method of classifying test data, the test data comprising a plurality of biomarker measures of each of a set of biomarkers, the method comprising: (i) accessing, using at least one processor, an electronically stored set of training data vectors, each training data vector representing an individual human and comprising a biomarker measure of each biomarker of the set of biomarkers for the respective human, each training data vector further comprising a classification with respect to the presence or absence of diagnosed NSCLC in the respective human; (ii) training an electronic representation of a classification system, using the electronically stored set of training data vectors; (iii) receiving, at the at least one processor, test data comprising a plurality of biomarker measures for the set of biomarkers in a human test subject; (iv) evaluating, using the at least one processor, the test data using the electronic representation of the classification system; and (v) outputting a classification of the human test subject concerning the likelihood of presence or development of non-small cell lung cancer in the subject based on the evaluating step, wherein the set of biomarkers comprises at least nine (9) biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4.

In preferred embodiments, the test data comprises two or more replicate data vectors each comprising individual determinations of biomarker measures for the plurality of biomarkers in a physiological sample from a human subject, in which case, the sample may be classified as likely for the presence of development of NSCLC if any one of the replicate data vectors is classified positive for NSCLC according to any one of the classifiers in the classification system. Optionally, the test data and each training data vector further comprises at least one additional characteristic selected from the group consisting of the sex, race, ethnicity, and/or national origin, age and smoking status of the individual human.

The set of biomarkers for the various modes of this invention may comprise 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 biomarkers.

The biomarker measures are proportional to the respective concentration levels of biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, CYFRA-21-1, MIF, sICAM-1, SAA, or a combination thereof, in a physiological sample that is a biological fluid. Alternatively, the biomarker measures may be proportional to the respective concentration levels of biomarkers selected from the group consisting of IL-8, sTNFRII, MMP-9, TNFRI, CXCL9-MIG, Resistin, SAA, MPO, PDGF-AB-BB, MMP-7, GRO, MIF, MCP-1, CEA, CYFRA-21-1, Leptin, IL-2, IL-10, and NSE. In another alternative embodiment, the biomarker measures are proportional to the respective concentration levels of biomarkers selected from the group consisting of IL-8, sTNFRII, MMP-9, TNFRI, CXCL9-MIG, Resistin, SAA, MPO, PDGF-AB-BB, MMP-7, GRO, MIF, MCP-1, CEA, CYFRA-21-1, Leptin, IL-2, and IL-10. In yet another alternative embodiment, the biomarker measures are proportional to the respective concentration levels of biomarkers selected from the group consisting of IL-8, MMP-9, sTNFRII, TNFRI, MMP7, Resistin, MPO, NSE, GRO, CEA, CXCL9, MIF, IL-2, SAA, IL-16, PDFG-AB/BB, or a combination thereof, and the physiological sample is a biological fluid. In still another alternative embodiment, the biomarker measures are proportional to the respective concentration levels of biomarkers selected from the group consisting of IL-8, sTNFRII, MMP-9, TNFRI, CXCL9-MIG, Resistin, SAA, MPO, PDGF-AB-BB, MMP-7, GRO, MIF, MCP-1, CEA, CYFRA-21-1, Leptin, and IL-2. In yet another alternative embodiment, the biomarker measures are proportional to the respective concentration levels of biomarkers selected from the group consisting of IL-8, sTNFRII, MMP-9, TNFRI, CXCL9-MIG, Resistin, SAA, MPO, PDGF-AB-BB, MMP-7, GRO, MIF, MCP-1, CEA, CYFRA-21-1, and Leptin. In still another alternative embodiment, the biomarkers measures are proportional to the respective concentration levels of biomarkers, are selected from the group consisting of IL-8, MMP-9, sTNFRII, TNFRI, Resistin, MPO, NSE, GRO, CEA, CXCL9, IL-2, SAA, PDFG-AB/BB, or a combination thereof, and the physiological sample is a biological fluid. In yet another alternative embodiment, the biomarker measures are proportional to the respective concentration levels of biomarkers selected from the group consisting of IL-8, sTNFRII, MMP-9, TNFRI, CXCL9-MIG, Resistin, SAA, MPO, PDGF-AB-BB, and MMP-7.

The method of this invention may further comprise determining the biomarker measure in a physiological sample from a subject. Typically the various biomarkers are peptides, proteins, peptides and proteins bearing post-translational modifications, or a combination thereof, and the biological fluid is blood, serum, plasma, or a mixture thereof. In a preferred version of any mode of this invention, the classification system is Random Forest, and preferably the Random Forest classifier comprises 5, 10, 15, 20, 25, 30, 40, 50, 75 or 100 individual trees.

Typically, in the method of this invention, the subject is human, who may be a female or a male human. In preferred embodiments of this invention, the subject exhibits at least one lung nodule detectable by computerized tomography scan. For example, the method may further comprise testing for lung nodules by low-dose computerized tomography. In alternative embodiments, the subject is at-risk for NSCLC, and/or the method may further comprise the step of treating the subject for NSCLC. In a particularly preferred embodiment of this invention, the subject (or patient) is 45 years old or older, is a long-term smoker, has been diagnosed with indeterminate nodules in the lungs, or a combination thereof.

In a particularly preferred mode, this invention provides a method of classifying test data, the test data comprising a plurality of biomarker measures of each of a set of biomarkers, the method comprising: (a) receiving, on at least one processor, test data comprising a biomarker measure for each biomarker of a set of biomarkers in a physiological sample from a human test subject; (b) evaluating, using the at least one processor, the test data using a classifier which is an electronic representation of a classification system, each said classifier trained using an electronically stored set of training data vectors, each training data vector representing an individual human and comprising a biomarker measure of each biomarker of the set of biomarkers for the respective human, each training data vector further comprising a classification with respect to the presence or absence of diagnosed NSCLC in the respective human; and (c) outputting, using the at least one processor, a classification of the sample from the human test subject concerning the likelihood of presence or development of NSCLC in the subject based on the evaluating step, wherein said set of biomarkers comprises at least eight (8) biomarkers selected from the group consisting of IL-8, sTNFRII, MMP-9, TNFRI, CXCL9-MIG, Resistin, SAA, MPO, PDGF-AB-BB, MMP-7, GRO, MIF, MCP-1, CEA, CYFRA-21-1, Leptin, IL-2, IL-10, and NSE.

In an alternative mode, this invention provides a system for classifying test data, the test data comprising a plurality of biomarker measures of each of a set of biomarkers, the system comprising: at least one processor coupled to electronic storage means comprising an electronic representation of a classifier, said classifier trained using an electronically stored set of training data vectors, according to any one of the preceding claims, said process configured to receive test data comprising a plurality of biomarker measures for the set of biomarkers in a human test subject, the at least one processor further configured to evaluate the test data using the electronic representation of the one or more classifiers and output a classification of the human test subject based on the evaluation, wherein said set of biomarkers comprises at least nine (9) biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4. Alternatively, this invention provides a non-transitory computer-readable storage medium with an executable program stored thereon, wherein the program instructs a microprocessor to perform the following steps (i) receiving biomarker measures of a plurality of biomarkers in a physiological sample of the subject; and (ii) classifying the sample based on the biomarker measures, using a classification system and the at least one processor, wherein the classification of the sample is indicative of the likelihood of presence or development of non-small cell lung cancer (NSCLC) in the subject, wherein said set of biomarkers comprises at least nine (9) biomarkers selected from the group consisting of IL-8, NMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4.

The method of this invention may further comprise (a) obtaining a physiological sample from a subject; and (b) measuring in the sample a set of at least four biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4 to produce a biomarker measure. The method may comprise measuring in the sample a set of at least 4, 5, 6, 7, 8, 9, 10, 11, 12, 13, 14, 15, 16, 17, 18, 19, or 21 of the biomarkers. The biomarker measures may be indicative of non-small cell lung cancer. The biomarker measures may be indicative of early stage non-small cell lung cancer, preferably Stage I. In several embodiments, the subject may be at risk for non-small cell lung cancer.

The method of this invention may further comprise measuring in the sample a set of at least four biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4 in a physiological sample obtained from a subject to produce a biomarker measure. The method may comprise measuring in the sample a set of at least 4, 5, 6, 7, 8, 9, 10, 11, 12, 13, 14, 15, 16, 17, 18, 19, or 21 of the biomarkers. The biomarker measures may be indicative of non-small cell lung cancer. The biomarker measures may be indicative of early stage non-small cell lung cancer, preferably Stage I. In several embodiments, the subject may be at risk for non-small cell lung cancer.

In several embodiments, the biomarker measures may be measured by radio-immuno assay, enzyme-linked immunosorbent assay (ELISA), Q-Plex™ Multiplex Assays, liquid chromatography-mass spectrometry (LCMS), flow cytometry multiplex immunoassay, high pressure liquid chromatography with radiometric or spectrometric detection via absorbance of visible or ultraviolet light, mass spectrometric qualitative and quantitative analysis, western blotting, 1 or 2 dimensional gel electrophoresis with quantitative visualization by means of detection of radioactive, fluorescent or chemiluminescent probes or nuclei, antibody-based detection with absorptive or fluorescent photometry, quantitation by luminescence of any of a number of chemiluminescent reporter systems, enzymatic assays, immunoprecipitation or immuno-capture assays, solid and liquid phase immunoassays, quantitative multiplex immunoassay, protein arrays or chips, plate assays, printed array immunoassays, or a combination thereof. In preferred embodiments, the biomarker measures may be measured by immunoassay.

The invention also provides for a method for diagnosing Stage I non-small cell lung cancer comprising: (a) obtaining a physiological sample from a subject; (b) measuring in the sample a set of from four to thirty-three biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4 by immunoassay to produce biomarker measures; (c) receiving, on at least one processor, test data comprising the biomarker measure for each biomarker of a set of biomarkers in a physiological sample from a human test subject; (d) evaluating, using the at least one processor, the test data using a classifier which is an electronic representation of a classification system, each classifier trained using an electronically stored set of training data vectors, each training data vector representing an individual human and comprising the biomarker measure of each biomarker of the set of biomarkers for the respective human, each training data vector further comprising a classification with respect to the presence or absence of diagnosed NSCLC in the respective human; and (e) outputting, using the at least one processor, a classification of the sample from the human test subject concerning the likelihood of presence or development of NSCLC in the subject based on the evaluating step. In several embodiments, classification system may be selected from the group consisting of Random Forest, AdaBoost, Naive Bayes, Support Vector Machine, LASSO, Ridge Regression, Neural Net, Genetic Algorithms, Elastic Net, Gradient Boosting Tree, Bayesian Neural Network, k-Nearest Neighbor, or an ensemble thereof. The biomarkers may be peptides, proteins, peptides bearing post-translational modifications, proteins bearing post-translational modification, or a combination thereof. The physiological sample may be whole blood, blood plasma, blood serum, or a combination thereof.

The invention also provides for a method for diagnosing Stage I non-small cell lung cancer comprising measuring in the sample a set of at least four biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4 in a physiological sample obtained from a subject by immunoassay to produce biomarker measures; (c) receiving, on at least one processor, test data comprising the biomarker measure for each biomarker of a set of biomarkers in a physiological sample from a human test subject; (d) evaluating, using the at least one processor, the test data using a classifier which is an electronic representation of a classification system, each classifier trained using an electronically stored set of training data vectors, each training data vector representing an individual human and comprising the biomarker measure of each biomarker of the set of biomarkers for the respective human, each training data vector further comprising a classification with respect to the presence or absence of diagnosed NSCLC in the respective human; and (e) outputting, using the at least one processor, a classification of the sample from the human test subject concerning the likelihood of presence or development of NSCLC in the subject based on the evaluating step. In several embodiments, classification system may be selected from the group consisting of Random Forest, AdaBoost, Naive Bayes, Support Vector Machine, LASSO, Ridge Regression, Neural Net, Genetic Algorithms, Elastic Net, Gradient Boosting Tree, Bayesian Neural Network, k-Nearest Neighbor, or an ensemble thereof. The biomarkers may be peptides, proteins, peptides bearing post-translational modifications, proteins bearing post-translational modification, or a combination thereof. The physiological sample may be whole blood, blood plasma, blood serum, or a combination thereof.

In many embodiments, a method for detecting a plurality of biomarkers may comprise (a) obtaining a physiological sample from a subject; and (b) measuring in the sample a set of at least four biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4 to produce biomarker measures. The biomarker measures may be indicative of non-small cell lung cancer. The biomarker measures may be indicative of early stage non-small cell lung cancer, optionally Stage I non-small cell lung cancer. The biomarker measures may not be indicative of asthma, breast cancer, prostate cancer, pancreatic cancer, or a combination thereof. In many embodiments, the subject may be at risk for non-small cell lung cancer.

In many embodiments, a method for detecting a plurality of biomarkers may comprise measuring in the sample a set of at least four biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4 in a physiological sample obtained from a subject to produce biomarker measures. The biomarker measures may be indicative of non-small cell lung cancer. The biomarker measures may be indicative of early stage non-small cell lung cancer, optionally Stage I non-small cell lung cancer. The biomarker measures may not be indicative of asthma, breast cancer, prostate cancer, pancreatic cancer, or a combination thereof. In many embodiments, the subject may be at risk for non-small cell lung cancer.

The set of at least four biomarkers may be selected from the group consisting of IL-8, MMP-9, sTNFRII, TNFRI, MMP-7, IL-5, Resistin, IL-10, MPO, NSE, MCP-1, GRO-Pan, CEA, Leptin, CXCL9/1MIG, CYFRA 21-1, MIF, sICAM-1, SAA, IL-2, and PDGF-AB/BB. The set of at least four biomarkers may be selected from the group consisting of IL-8, MMP-9, sTNFRII, TNFRI, MMP-7, IL-5, Resistin, IL-10, MPO, NSE, MCP-1, GRO-Pan, CEA, Leptin, CXCL9/MIG, CYFRA 21-1, MIF, sICAM-1, and SAA. The set of at least four biomarkers may be selected from the group consisting of IL-8, MMP-9, sTNFRII, TNFRI, Resistin, MPO, NSE, GRO-Pan, CEA, CXCL9/MIG, SAA, IL-2, and PDGF-AB/BB.

In several embodiments, the set may comprise at least 4, 5, 6, 7, 8, 9, 10, 11, 12, 13, 14, 15, 16, 17, 18, 19, 20, or 21 biomarkers.

In several embodiments, the biomarkers may be peptides, proteins, peptides bearing post-translational modifications, proteins bearing post-translational modification, or a combination thereof.

In several embodiments, the physiological sample may be whole blood, blood plasma, blood serum, or a combination thereof.

In several embodiments, the method may further comprise (a) receiving, on at least one processor, test data comprising the biomarker measure for each biomarker of a set of biomarkers in a physiological sample from a human test subject; (b) evaluating, using the at least one processor, the test data using a classifier which is an electronic representation of a classification system, each classifier trained using an electronically stored set of training data vectors, each training data vector representing an individual human and comprising the biomarker measure of each biomarker of the set of biomarkers for the respective human, each training data vector further comprising a classification with respect to the presence or absence of diagnosed NSCLC in the respective human; and (c) outputting, using the at least one processor, a classification of the sample from the human test subject concerning the likelihood of presence or development of NSCLC in the subject based on the evaluating step.

In many preferred embodiments, the classification system may be one or more algorithms selected from the group consisting of Random Forest, AdaBoost, Naive Bayes, Support Vector Machine, LASSO, Ridge Regression, Neural Net, Genetic Algorithms, Elastic Net, Gradient Boosting Tree, Bayesian Neural Network, k-Nearest Neighbor, or an ensemble thereof.

The invention also provides for a method of determining the existence of non-small cell lung cancer early in disease progression by measuring expression levels of a set of biomarkers in a subject comprising: determining biomarker measures of a set of biomarkers by immunoassay in a physiological sample, wherein the set of biomarkers comprise at least four biomarkers selected from the group consisting of IL-8, MMP-9, sTNFRII, TNFRI, MMP7, IL-5, Resistin, IL-10, MPO, NSE, MCP-1, GRO, CEA, leptin, CXCL9, HGF, sCD40L, CYFRA-21-1, sFasL, RANTES, IL-7, MIF, sICAM-1, IL-2, SAA, IL-16, IL-9, PDFG-AB/BB, sEFGR, LIF, IL-12p70, CA125, and IL-4; classifying the sample with respect to the presence or development of non-small cell lung cancer in the subject using the set of biomarker measures in a classification system.

In many embodiments, the set of at least four biomarkers may be selected from the group consisting of IL-8, MMP-9, sTNFRII, TNFRI, 1L-5, Resistin, IL-10, MPO, NSE, MCP-1, GRO-Pan, CEA, Leptin, CXCL9/MIG, CYFRA 21-1, MIF, sICAM-1, SAA, IL-2, and PDGF-AB/BB.

In many embodiments, the set of at least four biomarkers may be selected from the group consisting of IL-8, MMP-9, sTNFRII, TNFRI, MMP-7, IL-5, Resistin, IL-10, MPO, NSE, MCP-1, GRO-Pan, CEA, Leptin, CXCL9/MIG, CYFRA 21-1, MIF, sICAM-1, and SAA.

In many embodiments, the set of at least four biomarkers may be selected from the group consisting of IL-8, MMP-9, sTNFRII, TNFRI, Resistin, MPO, NSE, GRO-Pan, CEA, CXCL9/MIG, SAA, IL-2, and PDGF-AB/BB.

In any of the foregoing embodiments, the set may comprise at least 4, 5, 6, 7, 8, 9, 10, 11, 12, 13, 14, 15, 16, 17, 18, or 19 biomarkers.

In any of the foregoing embodiments, the classification system may be selected from the group consisting of Random Forest, AdaBoost, Naive Bayes, Support Vector Machine, LASSO, Ridge Regression, Neural Net, Genetic Algorithms, Elastic Net, Gradient Boosting Tree, Bayesian Neural Network, k-Nearest Neighbor, or an ensemble thereof.

In any of the foregoing embodiments of the invention, the biomarkers may be peptides, proteins, peptides bearing post-translational modifications, proteins bearing post-translational modification, or a combination thereof.

In any of the foregoing embodiments of the invention, the physiological sample may be whole blood, blood plasma, blood serum, or a combination thereof.

In any of the foregoing embodiments of the invention, the biological fluid may be whole blood, blood plasma, blood serum, sputum, urine, sweat, lymph, and alveolar lavage.

The methods and systems provided herein are capable of diagnosing and predicting lung pathologies (e.g., cancerous) typically with over 90% accuracy (e.g., total correct over total tested). These results provide a significant advancement over currently available methods for diagnosing and predicting non-small cell lung cancer.

DETAILED DESCRIPTION OF THE INVENTION

Figure 1A:
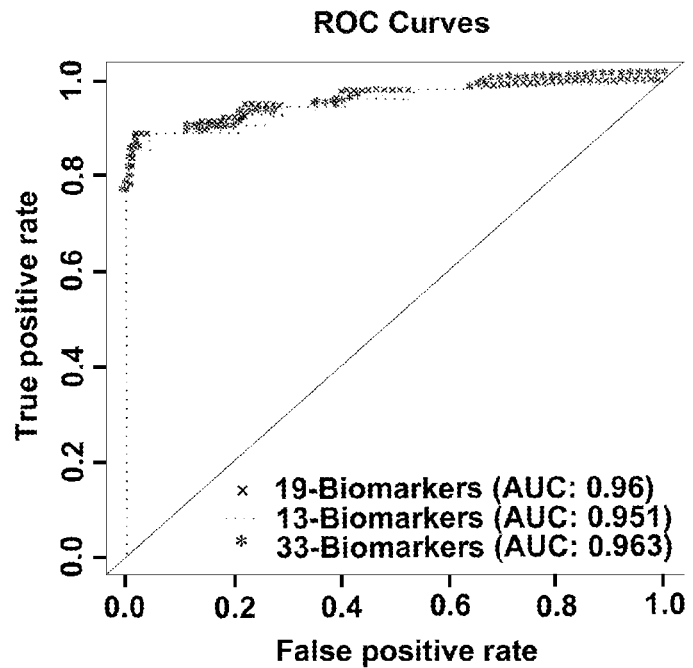
FIG. 1A-B depicts the ROC Curves for 33, 19 and 13 biomarkers. This shows that the two models have good discriminatory ability between NSCLC (FIG. 1A) and non-NSCLC cancers (FIG. 1B).

The invention relates to various methods of detection, identification, and diagnosis of lung disease using biomarkers. These methods involve determining biomarker measures of specific biomarkers and using these biomarker measures in a classification system to determine the likelihood that an individual has non-small cell lung cancer. The invention also provides for kits comprising detection agents for detecting these biomarkers, or means for determining the biomarker measures of these biomarkers, as components of systems for assisting in determining the likelihood of non-small cell lung cancer. Exemplary biomarkers were identified by measuring the expression levels of eighty-two selected biomarkers in the plasma of patients from populations who that have shown diagnostic potential for early stage lung cancer. This method is detailed in Example 1.

An in vitro Diagnostic Multivariate Index Assay (IVDMIA) that employs an algorithm using multiple protein biomarkers and the patient's demographic data to yield a qualitative single score classifier of either a "Yes" or "No" for the presence of early stage non-small cell lung cancer is described herein. The IVDMIA Test described in this example may be used in an adjunctive risk stratification model for patients with nodules found in the lungs during a primary diagnostic test, i.e., a CT scan, when it is unclear as to whether the nodule is cancerous or not. This test can assist physicians in the selection of appropriate subsequent diagnostic procedures for Non-Small Cell Lung Cancer (NSCLC). For example, individuals who are at a high risk of developing NSCLC, such as smokers over forty-five years old, may be screened using this test.

Definitions

As used herein, a "biomarker" or "marker" refer broadly to a biological molecule that can be objectively measured as a characteristic indicator of the physiological status of a biological system. For purposes of the present disclosure, biological molecules include ions, small molecules, peptides, proteins, peptides and proteins bearing post-translational modifications, nucleosides, nucleotides and polynucleotides including RNA and DNA, glycoproteins, lipoproteins, as well as various covalent and non-covalent modifications of these types of molecules. Biological molecules include any of these entities native to, characteristic of, and/or essential to the function of a biological system. The majority of biomarkers are polypeptides, although they may also be mRNA or modified mRNA which represents the pre-translation form of a gene product expressed as the polypeptide, or they may include post-translational modifications of the polypeptide.

As used herein, a "biomarker measure" refers broadly to information relating to a biomarker that is useful for characterizing the presence or absence of a disease. Such information may include measured values which are, or are proportional to, concentration, or that are otherwise provide qualitative or quantitative indications of expression of the biomarker in tissues or biologic fluids. Each biomarker can be represented as a dimension in a vector space, where each vector is a multi-dimensional vector in the vector space and includes a plurality of biomarker measures associated with a particular subject.

As used herein, "classifier" refers broadly to a machine learning algorithm such as support vector machine(s), AdaBoost classifier(s), penalized logistic regression, elastic nets, regression tree system(s), gradient tree boosting system(s), naïve Bayes classifier(s), neural nets, Bayesian neural nets, k-nearest neighbor classifier(s), and random forests. This invention contemplates methods using any of the listed classifiers, as well as use of more than one of the classifiers in combination.

As used herein, "classification system" refers broadly to a machine learning system executing at least one classifier.

As used herein, "subset" is a proper subset and "superset" is a proper superset.

As used herein, a "subject" refers broadly to any animal, but is preferably a mammal, such as, for example, a human. In many embodiments, the subject were a human patient having, or at-risk of having, a lung disease.

As used herein, a "physiological sample" refers broadly to samples from biological fluids and tissues. Biological fluids include whole blood, blood plasma, blood serum, sputum, urine, sweat, lymph, and alveolar lavage. Tissue samples include biopsies from solid lung tissue or other solid tissues, lymph node biopsy tissues, biopsies of metastatic foci. Methods of obtaining physiological samples are described in the art.

As used herein, "detection agents" refers broadly to reagents and systems that specifically detect the biomarkers described herein. Detection agents include reagents such as antibodies, nucleic acid probes, aptamers, lectins, or other reagents that have specific affinity for a particular marker or markers sufficient to discriminate between the particular marker and other markers which might be in samples of interest, and systems such as sensors, including sensors making use of bound or otherwise immobilized reagents as described above.

As used herein, "Classification and Regression Trees (CART)," refers broadly to a method to create decision trees based on recursively partitioning a data space so as to optimize some metric, usually model performance.

As used herein, "AdaBoost," refers broadly to a bagging method that iteratively fits CARTs re-weighting observations by the errors made at the previous iteration.

As used herein, "False Positive (FP)," refers broadly to an error in which the algorithm test result indicates the presence of a disease when the disease is actually absent.

As used herein, "False Negative (FN)," refers broadly to an error in which the algorithm test result indicates the absence of a disease when the disease is actually present.

As used herein, "Genetic Algorithm," refers broadly to an algorithm that mimics genetic mutation used to optimize a function (e.g., model performance).

As used herein, "Intra-assay Precision," reflects repeatability of the assay using measurements within a plate for each individual plasma sample. Intra-assay % CV was calculated by taking an average Mean (M) MFI of all replicates for the individual plasma divided by the standard deviation (SD) of all replicates and multiplied by 100, % CV=(SD/M)*100. Lower concentrations may result in poorer precision.

As used herein, "Inter-assay Precision," reflects reproducibility of the assay using measurements from different plates, days, and operators for each individual plasma sample. Inter-assay % CV was calculated by taking an average MFI of all replicates for the individual plasma from all runs divided by the standard deviation (SD) of all replicates and multiplied by 100, % CV=(SD/M)*100. Lower concentrations may result in poorer precision.

As used herein, "L1 Norm," is the sum of the absolute values of the elements of a vector.

As used herein, "L2 Norm," is the square root of the sum of the squares of the elements of a vector.

As used herein, "Limit of Detection (LOD)," is calculated as Average Median Measured Value of the Blanks plus 2 SD, LOD=M+2 SD. This value is lower than or equal to the LLOQ and is not necessarily quantifiable.

As used herein, "Lower Limit of Quantitation (LLOQ)," is the lowest concentration of analyte in a sample that can be quantitatively determined with suitable precision and accuracy. In most instances LLOQ exceeds LOD but it is possible for the two values to be equal. The parameters for the determination of LLOQ are within 20% CV and a recovery range of +20% (80-120%).

As used herein, "Percent of Coefficient of Variation (% CV)," is calculated as follows: Standard Deviation (SD) divided by the Mean (M) and expressed in percentage.

As used herein, "Negative Predictive Value (NPV)," is the number of true negatives (TN) divided by the number of true negatives (TN) plus the number of false negatives (FP), TP/(TN+FN).

As used herein, "Positive Predictive Value (PPV)," is the number of true positives (TP) divided by the number of true positives (TP) plus the number of false positives (FP), TP/(TP+FP).

As used herein, "Precision," is used to express the spread between a series of measurements and includes repeatability (intra-assay) and reproducibility (inter-assay).

As used herein, "Perceptron," refers to a method to separate groups of observations based on the dot product of a set of weights and the vector of observed values.

As used herein, "Neural Net," is a classification method that chains together perceptron-like objects to create a classifier.

As used herein, "LASSO," refers broadly to a method for performing linear regression with a constraint on the L1 norm of the vector of regression coefficients.

As used herein, "Random Forest," refers broadly to a bagging method that fits CARTs based on samples from the dataset that the model is trained on.

As used herein, "Ridge Regression," refers broadly to a method for performing linear regression with a constraint on the L2 norm of the vector of regression coefficients.

As used herein, "Elastic Net," refers broadly to a method for performing linear regression with a constraint comprised of a linear combination of the L1 norm and L2 norm of the vector of regression coefficients.

As used herein, "Sensitivity," is the probability of a positive result for a patient with NSCLC. Sensitivity is calculated as the number of true positives (TP) divided by total number of actual NSCLC patients, or number of true positives (TP) plus the number of false negatives (FN); Sensitivity=TP/(TP+FN).

As used herein, "Specificity," is the probability that the patient does not have NSCLC. Specificity is calculated as the number of true negatives (TN) divided by total number of actual Non-NSCLC patients, or number of true negatives (TN) plus the number of false positives (FP); Specificity=TN/(TN+FP).

As used herein, "Standard of Deviation (SD)," is the spread in individual data points (i.e., in a replicate group) to reflect the uncertainty of a single measurement.

As used herein, "Training Set," is the set of samples that are used to train and develop a machine learning system, such as the algorithm of this invention.

As used herein, "True Negative (TN)," is the algorithm test result indicates the absence of a disease when the disease is actually absent.

As used herein, "True Positive (TP)," is the algorithm test result indicates the presence of a disease when the disease is actually present.

As used herein, "Upper Limit of Quantitation (ULOQ)," is the highest concentration of analyte in a sample that can be quantitatively determined with suitable precision and accuracy. The parameters for the determination of ULOQ are within 20% CV and a recovery range of ±20% (80-120%).

As used herein, "Validation Set," is the set of samples that are blinded and used to confirm the functionality of the algorithm developed according to this invention. This is also known as the Blind Set.

Determining Biomarker Measures

A biomarker measure is information that generally relates to a quantitative measurement of an expression product, which is typically a protein or polypeptide. The invention contemplates determining the biomarker measure at the protein level (which may include post-translational modification). In particular, the invention contemplates determining changes in biomarker concentrations reflected in an increase or decrease in the level of transcription, translation, post-transcriptional modification, or the extent or degree of degradation of protein, where these changes are associated with a particular disease state or disease progression.

Many proteins that are expressed by a normal subject were expressed to a different extent (greater or lesser) in subjects having a lung disease, such as non-small cell lung cancer. One of skill in the art will appreciate that most diseases manifest changes in multiple, different biomarkers. As such, disease may be characterized by a pattern of expression of a plurality of markers. The determination of expression levels for a plurality of biomarkers facilitates the observation of a pattern of expression, and such patterns provide for more sensitive and more accurate diagnoses than detection of individual biomarkers. A pattern may comprise abnormal elevation of some particular biomarkers simultaneously with abnormal reduction in other particular biomarkers.

In accordance with this invention, physiological samples are collected from subjects in a manner which ensures that the biomarker measure in the sample is proportional to the concentration of that biomarker in the subject from which the sample is collected. Measurements are made so that the measured value is proportional to the concentration of the biomarker in the sample. Selecting sampling techniques and measurement techniques which meet these requirements is within ordinary skill of the art.

The skilled person will understand that a variety of methods for determining biomarker measures are known in the art for individual biomarkers. See Instrumental Methods of Analysis, Seventh Edition, 1988. Such determination may be performed in a multiplex or matrix-based format such as a multiplexed immunoassay.

Numerous methods of determining biomarker measures are known in the art. Means for such determination include, but are not limited to, radio-immuno assay, enzyme-linked immunosorbent assay (ELISA), Q-Plex™ Multiplex Assays, liquid chromatography-mass spectrometry (LCMS), flow cytometry multiplex immunoassay, high pressure liquid chromatography with radiometric or spectrometric detection via absorbance of visible or ultraviolet light, mass spectrometric qualitative and quantitative analysis, western blotting, 1 or 2 dimensional gel electrophoresis with quantitative visualization by means of detection of radioactive, fluorescent or chemiluminescent probes or nuclei, antibody-based detection with absorptive or fluorescent photometry, quantitation by luminescence of any of a number of chemiluminescent reporter systems, enzymatic assays, immunoprecipitation or immuno-capture assays, solid and liquid phase immunoassays, protein arrays or chips, plate assays, assays that use molecules having binding affinity that permit discrimination such as aptamers and molecular imprinted polymers, and any other quantitative analytical determination of the concentration of a biomarker by any other suitable technique, as well as instrumental actuation of any of the described detection techniques or instrumentation. Particularly preferred methods for determining biomarker measures include printed array immunoassays.

The step of determining biomarker measures may be performed by any means known in the art, especially those means discussed herein. In preferred embodiments, the step of determining biomarker measures comprises performing immunoassays with antibodies. One of skill in the art would readily be able to select appropriate antibodies for use in the present invention. The antibody chosen is preferably selective for an antigen of interest (i.e., selective for the particular biomarker) possesses a high binding specificity for said antigen, and has minimal cross-reactivity with other antigens. The ability of an antibody to bind to an antigen of interest may be determined, for example, by known methods such as enzyme-linked immunosorbent assay (ELISA), flow cytometry, and immunohistochemistry. Furthermore, the antibody should have a relatively high binding specificity for the antigen of interest. The binding specificity of the antibody may be determined by known methods such as immunoprecipitation or by an in vitro binding assay, such as radioimmunoassay (RIA) or ELISA. Disclosure of methods for selecting antibodies capable of binding antigens of interest with high binding specificity and minimal cross-reactivity are provided, for example, in U.S. Pat. No. 7,288,249.

In a preferred embodiment, a single molecule array format may be used. In this method, single protein molecules are captured and labelled on beads using standard immunosorbent assay reagents. Thousands of beads (with or without an immunoconjugate) are mixed with enzyme substrate and loaded into individual femtoliter-sized wells, and sealed with oil. The fluorophore concentration of each bead is digitally counted to determine if it is bound to the target analyte or not. Disclosures of such methods are provided, for example, in U.S. Pat. No. 8,236,574.

Biomarker measures of biomarkers indicative of lung disease may be used as input for a classification system, which includes the classifiers as described herein, alone or in combination. Each biomarker can be represented as a dimension in a vector space, where each vector is made up of a plurality of biomarker measures associated with a particular subject. Thus, the dimensionality of the vector space corresponds to the size of the set of biomarkers. Patterns of biomarker measures of a plurality of biomarkers may be used in various diagnostic and prognostic methods. This invention provides such methods. Exemplary methods include using classifiers such as support vector machines, AdaBoost, penalized logistic regression, regression tree system(s), naïve Bayes classifier(s), neural nets, k-nearest neighbor classifier(s), random forests, or any combination thereof.

Classification Systems

The invention relates to, among other things, predicting lung pathologies as cancerous based on multiple, continuously distributed biomarkers. For some classification systems using classifiers (e.g., support vector machines. AdaBoost, penalized logistic regression, regression tree system(s), naïve Bayes classifier(s), neural nets, k-nearest neighbor classifier(s), random forests, or any combination thereof), prediction may be a multi-step process (e.g., a two-step process, a three-step process, etc.).

As used herein, the classifications systems described may include computer executable software, firmware, hardware, or various combinations thereof. For example, the classification systems may include reference to a processor and supporting data storage. Further, the classification systems may be implemented across multiple devices or other components local or remote to one another. The classification systems may be implemented in a centralized system, or as a distributed system for additional scalability. Moreover, any reference to software may include non-transitory computer readable media that when executed on a computer, causes the computer to perform a series of steps.

The classification systems described herein may include data storage such as network accessible storage, local storage, remote storage, or a combination thereof. Data storage may utilize a redundant array of inexpensive disks ("RAID"), tape, disk, a storage area network ("SAN"), an internet small computer systems interface ("iSCSI") SAN, a Fibre Channel SAN, a common Internet File System ("CIFS"), network attached storage ("NAS"), a network file system ("NFS"), or other computer accessible storage. In one or more embodiments, data storage may be a database, such as an Oracle database, a Microsoft SQL Server database, a DB2 database, a MySQL database, a Sybase database, an object oriented database, a hierarchical database, or other database. Data storage may utilize flat file structures for storage of data.

In the first step, a classifier is used to describe a predetermined set of data. This is the "learning step" and is carried out on "training" data.

The training database is a computer-implemented store of data reflecting a plurality of biomarker measures for a plurality of humans in association with a classification with respect to a disease state of each respective human. The format of the stored data may be as a flat file, database, table, or any other retrievable data storage format known in the art. In an exemplary embodiment, the test data is stored as a plurality of vectors, each vector corresponding to an individual human, each vector including a plurality of biomarker measures for a plurality of biomarkers together with a classification with respect to a disease state of the human. Typically, each vector contains an entry for each biomarker measure in the plurality of biomarker measures. The training database may be linked to a network, such as the internet, such that its contents may be retrieved remotely by authorized entities (e.g., human users or computer programs). Alternately, the training database may be located in a network-isolated computer.

In the second step, which is optional, the classifier is applied in a "validation" database and various measures of accuracy, including sensitivity and specificity, are observed. In an exemplary embodiment, only a portion of the training database is used for the learning step, and the remaining portion of the training database is used as the validation database. In the third step, biomarker measures from a subject are submitted to the classification system, which outputs a calculated classification (e.g., disease state) for the subject.

Several methods are known in the art for classification, including using classifiers such as support vector machines, AdaBoost, decisions trees, Bayesian classifiers, Bayesian belief networks, naïve Bayes classifiers, k-nearest neighbor classifiers, case-based reasoning, penalized logistic regression, neural nets, random forests, or any combination thereof (See e.g., Han J Kamber M, 2006, Chapter 6, *Data Mining, Concepts and Techniques,* 2nd Ed. Elsevier: Amsterdam.). As described herein, any classifier or combination of classifiers may be used in a classification system.

Classifiers

There are many possible classifiers that could be used on the data. By way of non-limiting example, and as discussed below, classifiers such as support vector machines, genetic algorithms, penalized logistic regression, LASSO, ridge regression, naïve Bayes classifiers, classification trees, k-nearest neighbor classifiers, neural nets, elastic nets, Bayesian neural networks, Random Forests, gradient boosting trees, and/or AdaBoost may be used to classify the data. As discussed herein, the data may be used to train a classifier.

Classification Trees

A classification tree is an easily interpretable classifier with built in feature selection. A classification tree recursively splits the data space in such a way so as to maximize the proportion of observations from one class in each subspace.

The process of recursively splitting the data space creates a binary tree with a condition that is tested at each vertex. A new observation is classified by following the branches of the tree until a leaf is reached. At each leaf, a probability is assigned to the observation that it belongs to a given class. The class with the highest probability is the one to which the new observation is classified.

Classification trees are essentially a decision tree whose attributes are framed in the language of statistics. They are highly flexible but very noisy (the variance of the error is large compared to other methods).

Tools for implementing classification trees as discussed herein are available for the statistical software computing language and environment, R. For example, the R package "tree," version 1.0-28, includes tools for creating, processing and utilizing classification trees.

Random Forests

Classification trees are typically noisy. Random forests attempt to reduce this noise by taking the average of many trees. The result is a classifier whose error has reduced variance compared to a classification tree.

To grow a forest, the following algorithm is used:
1. For b=1 to B, where B is the number of trees to be grown in the forest,
   a. Draw a bootstrap sample[1].
   b. Grow a classification tree, $T_b$, on the bootstrap sample.
2. Output the set $\{T_b\}$. This set is the random forest.

[1] A bootstrap sample is a sample drawn with replacement from the observed data with the same number of observations as the observed data.

To classify a new observation using the random forest, classify the new observation using each classification tree in the random forest. The class to which the new observation is classified most often amongst the classification trees is the class to which the random forest classifies the new observation.

Random forests reduce many of the problems found in classification trees but at the price of interpretability.

Tools for implementing random forests as discussed herein are available for the statistical software computing language and environment, R. For example, the R package "randomForest," version 4.6-2, includes tools for creating, processing and utilizing random forests.

AdaBoost (Adaptive Boosting)

AdaBoost provides a way to classify each of n subjects into two or more[2] disease categories based on one k-dimensional vector (called a k-tuple) of measurements per subject. AdaBoost takes a series of "weak" classifiers that have poor, though better than random, predictive performance[3] and combines them to create a superior classifier. The weak classifiers that AdaBoost uses are classification and regression trees (CARTs). CARTs recursively partition the dataspace into regions in which all new observations that lie within that region are assigned a certain category label. AdaBoost builds a series of CARTs based on weighted versions of the dataset whose weights depend on the performance of the classifier at the previous iteration (Han J & Kamber M, (2006). Data Mining, Concepts and Techniques, 2nd Ed. Elsevier: Amsterdam).

[2] AdaBoost technically works only when there are two categories to which the observation can belong. For g>2 categories, (g/2) models must be created that classify observations as belonging to a group of not. The results from these models can then be combined to predict the group membership of the particular observation.

[3] Predictive performance in this context is defined as the proportion of observations misclassified.

Methods of Classifying Data Using Classification System(s)

The invention provides for methods of classifying data (test data, i.e., biomarker measures) obtained from an individual. These methods involve preparing or obtaining training data, as well as evaluating test data obtained from an individual (as compared to the training data), using one of the classification systems including at least one classifier as described above. Preferred classification systems use classifiers such as learning machines, including, for example support vector machines (SVM), AdaBoost, penalized logistic regression, naïve Bayes classifiers, classification trees, k-nearest neighbor classifiers, neural nets, random forests, and/or a combination thereof. The classification system outputs a classification of the individual based on the test data.

Particularly preferred for the present invention is an ensemble method used on a classification system, which combines multiple classifiers. For example, an ensemble method may include SVM, AdaBoost, penalized logistic regression, naïve Bayes classifiers, classification trees, k-nearest neighbor classifiers, neural nets, random forests, or any combination thereof, in order to make a prediction regarding disease pathology (e.g., NSCLC or normal). The ensemble method was developed to take advantage of the benefits provided by each of the classifiers, and replicate measurements of each plasma specimen.

The biomarker measures for each of the biomarkers in each subject's plasma are obtained for multiple samples. Typically, a plasma sample is collected and a full complement of biomarker measures are obtained for each sample. Each subject may be predicted as having a disease state (e.g., as NSCLC or normal) based on each of the replicate measurements (e.g., duplicate, triplicate) using a classification system including at least one classifier, yielding multiple predictions (e.g., four predictions, six predictions). In the preferred mode of this invention, the ensemble methodology may predict the subject to have NSCLC if at least one of the predictions was NSCLC and all of the other predictions predict the subject to be normal. The decision to predict a subject as having NSCLC if only one of the predictions from the classifier(s) is positive for NSCLC was made in order for the ensemble methodology to be as conservative as possible. In other words, this test was designed to err on the side of identifying a subject as having NSCLC in order to minimize the number of false negatives, which are more serious errors than false positive errors. The ensemble methodology may predict that the subject has, for example, NSCLC if at least two, or at least three, or at least four, or at least five, up to all of the predictions, are positive for NSCLC.

The test data may be any biomarker measures, such as plasma concentration measurements of a plurality of biomarkers. In one embodiment, the invention provides a method of classifying test data, the test data comprising biomarker measures that are a plurality of plasma concentration measures of each of a set of biomarkers comprising: (a) accessing an electronically stored set of training data vectors, each training data vector or k-tuple representing an individual human and comprising biomarker measures (i.e., a plasma concentration measure of each of the set of biomarkers) for the respective human for each replicate, the training data vector further comprising a classification with respect to a disease state of each respective human; (b) training an electronic representation of a classifier or an ensemble of classifiers as described herein using the electronically stored set of training data vectors; (c) receiving test data comprising a plurality of plasma concentration measures for a human test subject; (d) evaluating the test data using the electronic representation of the classifier and/or an ensemble of classifiers as described herein; and (e) outputting a classification of the human test subject based on the evaluating step. In another embodiment, the invention provides a method of classifying test data, the test data comprising biomarker measures that are a plurality of plasma concentration measures of each of a set of biomarkers comprising: (a) accessing an electronically stored set of training data vectors, each training data vector or k-tuple representing an individual human and comprising biomarker measures, such as a plasma concentration measure of each of the set of biomarkers for the respective human for each replicate, the training data further comprising a classification with respect to a disease state of each respective human; (b) using the electronically stored set of training data vectors to build a classifier and/or ensemble of classifiers; (c) receiving test data comprising a plurality of plasma concentration measures for a human test subject; (d) evaluating the test data using the classifier(s); and (e) outputting a classification of the human test subject based on the evaluating step. Alternatively, all (or any combination of) the replicates may be averaged to produce a single value for each biomarker for each subject. Outputting in accordance with this invention includes displaying information regarding the classification of the human test subject in an electronic display in human-readable form.

The classification with respect to a disease state may be the presence or absence of the disease state. The disease state according to this invention may be lung disease such as non-small cell lung cancer.

The set of training vectors may comprise at least 20, 25, 30, 35, 50, 75, 100, 125, 150, or more vectors.

It were understood that the methods of classifying data may be used in any of the methods described herein. In particular, the methods of classifying data described herein may be used in methods for physiological characterization, based in part on a classification according to this invention, and methods of diagnosing lung disease such as non-small cell lung cancer.

Classifying Data Using Reduced Numbers of Biomarkers

The invention also provides for methods of classifying data (such as test data obtained from an individual) that involve reduced sets of biomarkers. That is, training data may be thinned to exclude all but a subset of biomarker measures for a selected subset of biomarkers. Likewise, test data may be restricted to a subset of biomarker measures from the same selected set of biomarkers.

The biomarkers may be selected from the group consisting of bNGF, CA-125, CEA, CYFRA21-1, EGFR/HER1/ErbB1, GM-CSF, Granzyme B, Gro-alpha, ErbB2/HER2, HGF, IFN-a2, IFN-b, IFN-g, IL-10, IL-12p40, IL-12p70, IL-13, IL-15, IL-16, IL-17A, IL-17F, IL-1a, IL-1b, IL-1ra, IL-2, IL-20, IL-21, IL-22, IL-23p19, IL-27, IL-2ra, IL-3, IL-31, IL-4, IL-5, IL-6, IL-7, IL-8, IL-9, IP-10, I-TAC, Leptin, LIF, MCP-1, MCP-3, M-CSF, MIF, MIG, MIP-1a, MIP-1b, MIP-3a, MMP-7, MMP9, MPO, NSE, OPG, PAI-1, PDGF-AB/BB, PDGF, RANTES, Resistin, SAA, sCD40-ligand, SCF, SDF-1, SE-selectin, sFas ligand, sICAM-1, RANKL, TNFRI, TNFRII, sVCAM-1, TGF-α, TGF-β, TNF-α, TNF-β, TPO, TRAIL, TSP1, TSP2, VEGF-A, VEGF-C, and combinations thereof.

The biomarkers may be selected from the group consisting of IL-4, sEGFR, Leptin, NSE, MCP-1, GRO-pan, IL-10, IL-12P70, sCD40L, IL-7, IL-9, IL-2, IL-5, IL-8, IL-16, LIF, CXCL9/MIG, HGF, MIF, MMP-7, MMP-9, sFasL, CYFRA21-1, CA125, CEA, sICAM-1, MPO, RANTES, PDGF-AB/BB, Resistin, SAA, TNFRI, sTNFRII, and combinations thereof.

The biomarkers may be selected from the group consisting of IL-8, MMP-9, sTNFRII, TNFRI, MMP-7, IL-5, Resistin, IL-10, MPO, NSE, MCP-1, GRO-Pan, CEA, Leptin, CXCL9/MIG, CYFRA 21-1, MIF, sICAM-1, SAA, and combinations thereof.

The biomarkers may be selected from the group consisting of IL-8, MMP-9, sTNFRII, TNFRI, Resistin, MPO, NSE, GRO-Pan, CEA, CXCL9/MIG, IL-2, SAA, PDGF-AB/BB, and combinations thereof.

In one embodiment, the invention provides a method of classifying test data, the test data comprising biomarker measures that are a plurality of plasma concentration measures of each of a set of biomarkers comprising: (a) accessing an electronically stored set of training data vectors, each training data vector representing an individual human and comprising biomarker measures of each biomarker of the set of biomarkers for the respective human, each training data vector further comprising a classification with respect to a disease state of the respective human; (b) selecting a subset of biomarkers from the set of biomarkers; (c) training an electronic representation of a learning machine, such as a classifier or an ensemble of classifiers as described herein, using the data from the subset of biomarkers of the electronically stored set of training data vectors; (d) receiving test data comprising a plurality of plasma concentration measures for a human test subject related to the set of biomarkers in step (a); (e) evaluating the test data using the electronic representation of the learning machine; and (f) outputting a classification of the human test subject based on the evaluating step.

The methods, kits, and systems described herein may involve determining biomarker measures of a selected plurality of biomarkers. In a preferred mode, the method comprises determining biomarker measures of a subset of particular biomarkers of the biomarkers described in the Examples. Alternatively, the method comprises determining biomarker measures of a subset of at least two, three four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty-one, thirty-two, or thirty-three particular biomarkers of the biomarkers described in the Examples. Alternatively, the method comprises determining biomarker measures of a subset of at least eight, nine, ten, eleven, twelve, or thirteen particular biomarkers of the biomarkers described in the Examples. Alternatively, the method comprises determining biomarker measures of a subset of at least fourteen, fifteen, sixteen, seventeen, eighteen, nineteen, twenty, or more (e.g., thirty-three) particular biomarkers of the biomarkers described in the Examples. Alternatively, the methods, kits, and systems described herein may use a specific subset of biomarkers (e.g., at least thirteen, fifteen, nineteen, or thirty-three biomarkers), and one or more biomarkers from another subset of biomarkers (e.g., thirteen, fifteen, nineteen, or thirty-three biomarkers).

It is within the contemplation of this invention to contemporaneously determine biomarker measures of additional biomarkers whether or not associated with the disease of interest. Determination of these additional biomarker measures will not prevent the classification of a subject according to the present invention. However, the maximum number of biomarkers whose measures are included in the training data and test data of any of the methods of this invention may be, for example, six distinct biomarkers, ten distinct biomarkers, thirteen distinct biomarkers, fifteen distinct biomarkers, eighteen distinct biomarkers, twenty distinct biomarkers, or thirty-three distinct biomarkers. A skilled person would understand that the number of biomarkers should be limited to avoid inaccurate predictions due to overfitting. The subsets of biomarkers may be determined by using the methods of reduction described herein. A reduced model of particular subsets of biomarkers are described in the Examples.

In a preferred mode, the biomarkers are chosen from a computed subset which contains the biomarkers contributing a highest measure of model fit. As long as those biomarkers are included, the invention does not preclude the inclusion of a few additional biomarkers that do not necessarily contribute. Nor will including such additional biomarker measures in a classifying model preclude classification of test data, so long as the model is devised as described herein. In other embodiments, biomarker measures of no more than 4, 5, 6, 7, 8, 9, 10, 12, 15, 20, 25, 30, 35, 40 or 50 biomarkers are determined for the subject, and the same number of biomarkers are used in the training phase.

In another mode, the selected biomarkers are chosen from a computed subset from which biomarkers that contribute the least to a measure of model fit have been removed. As long as those selected biomarkers are included, the invention does not preclude the inclusion of a few additional biomarkers that do not necessarily contribute. Nor will including such additional biomarker measures in a classifying model preclude classification of test data, so long as the model is devised as described herein. In other embodiments, biomarker measures of no more than 4, 5, 6, 7, 8, 9, 10, 11, 12, 13, 14, 15, 16, 17, 18, 19, 20, 21, 22, 23, 24, 25, 30, 31, 32, 33, 34, 35, 40 or 50 biomarkers are determined for the subject, and the same number of biomarkers are used in the training phase.

It were understood that the methods of classifying data using reduced sets or subsets of biomarkers may be used in any of the methods described herein. In particular, the methods of classifying data using reduced numbers of biomarkers described herein may be used in methods for physiological characterization, based in part on a classification according to this invention, and methods of diagnosing lung disease such as non-small cell lung cancer. Biomarkers, other than the reduced number of biomarkers, may also be added. These additional biomarkers may or may not contribute to or enhance the diagnosis.

Lung Disease

The invention provides methods of diagnosing non-small cell lung cancer. These methods include determining biomarker measures of a plurality of biomarkers described herein, wherein the biomarkers are indicative of the presence or development of non-small lung cancer. For example, biomarker measures of biomarkers described herein may be used to assist in determining the extent of progression of non-small lung cancer, the presence of pre-cancerous lesions, or staging of non-small lung cancer. For example, the methods using the biomarker measures described herein may be used to diagnosis early stage (Stage I) non-small cell lung cancer. Also, the biomarker measures may be not indicative of asthma, breast cancer, prostate cancer, pancreatic cancer, or a combination thereof.

In particular embodiments, the subject is selected from those individuals who exhibit one or more symptoms of non-small cell lung cancer. Symptoms may include cough, shortness of breath, wheezing, chest pain, and hemoptysis; shoulder pain that travels down the outside of the arm or paralysis of the vocal cords leading to hoarseness; invasion of the esophagus may lead to difficulty swallowing. If a large airway is obstructed, collapse of a portion of the lung may occur and cause infections leading to abscesses or pneumonia. Metastases to the bones may produce excruciating pain. Metastases to the brain may cause neurologic symptoms including blurred vision, headaches, seizures, or symptoms commonly associated with stroke such as weakness or loss of sensation in parts of the body. Lung cancers often produce symptoms that result from production of hormone-like substances by the tumor cells. A common paraneoplastic syndrome seen in NSCLC is the production parathyroid hormone like substances which cause calcium in the bloodstream to be elevated.

Methods of Diagnosing Non-Small Cell Lung Cancer

The present invention is directed to methods of diagnosing non-small cell lung cancer in individuals in various populations as described below. In general, these methods rely on determining biomarker measures of particular biomarkers as described herein, and classifying the biomarker measures using a classification system that includes a classifier or an ensemble of classifiers as described herein.

A. Determination for the General Population

The invention provides for a method of diagnosing non-small cell lung cancer in a subject comprising, (a) obtaining a physiological sample of the subject; (b) determining biomarker measures of a plurality of biomarkers, as described herein, in said sample; and (c) classifying the sample based on the biomarker measures using a classification system, wherein the classification of the sample is indicative of the presence or development of non-small cell lung cancer in the subject.

In a preferred embodiment, the invention provides for methods of diagnosing non-small cell lung cancer in a subject comprising determining biomarker measures of a plurality of biomarkers in a physiological sample of the subject, wherein a pattern of expression of the plurality of markers are indicative of non-small cell lung cancer or correlate to a changes in a non-small cell lung cancer disease state (i.e., clinical or diagnostic stages). Preferably, the plurality of the biomarkers are selected based on analysis of training data via a machine learning algorithm such as a classifier or an ensemble of classifiers as described herein. The training data will include a plurality of biomarker measures for numerous subjects, as well as disease categorization for the individual subjects, and optionally, other characteristics of the subjects, such as sex, race, ethnicity, national origin, age, smoking history, and/or employment history In another preferred embodiment, patterns of expression correlate to an increased likelihood that a subject has or may have non-small cell lung cancer. Patterns of expression may be characterized by any technique known in the art for pattern recognition, such as those described as classifiers and/or an ensemble of classifiers as describe herein. The plurality of biomarkers may comprise any of the combinations of biomarkers described in the Examples.

In one embodiment, the subject is at-risk for non-small cell lung cancer. In another embodiment, the subject is selected from those individuals who exhibit one or more symptoms of non-small cell lung cancer.

B. Determination for the Male Population

The invention provides for a method of diagnosing non-small cell lung cancer in a male subject. Methods for these embodiments are similar to those described above, except that the subjects are male for both the training data and the sample.

C. Determination for the Female Population

The invention provides for a method of diagnosing non-small cell lung cancer in a female subject. Methods for these embodiments are similar to those described above, except that the subjects are female for both the training data and the sample.

D. Supplemental Analysis of Lung Nodules and Methods of Treatment

In a preferred mode, the classification methods of this invention may be used in conjunction with computerized tomography to provide an enhanced procedure for screening and early detection of NSCLC. In some embodiments, one of the classification methods described herein is applied to biomarker measures for a plurality of biomarkers in one or more physiological samples from a subject who has at least one lung nodule detected by CT scan. In a particular embodiment, the subject has at least one lung nodule with a diameter between six and twenty mm. Classification of the samples as NSCLC or Normal can assist in the ultimate diagnostic characterization of such patients. In alternative embodiments, after application of the classification methods to samples, those subjects whose samples are classified as NSCLC are selected for further testing by CT scan, and any nodules detected in such patients are treated according to the protocols for "high-risk" rather than "low-risk" patients. The preferred classification protocol for enhanced screening is the ensemble classification system, using replicate sampling (e.g., duplicate, triplicate), and those patients for whom at least one of the replicate samples is classified as "NSCLC" by a classifier or an ensemble of classifiers as described herein are considered "high-risk."

In other embodiments, the invention provides for methods of treatment based on the output of any of the classification methods described herein. For example, in one embodiment, the invention provides for a method of treating a subject for NSCLC following a classification of "NSCLC" using any of the classification methods described herein. Furthermore, as discussed in the preceding paragraph, the invention includes methods of treatment based on a diagnosis developed using the classification methods described herein in conjunction with additional analysis (e.g., CT scan).

Methods of Designing Systems for Characterization

E. General Population

The invention also provides a method for designing a system for diagnosing non-small cell lung cancer comprising (a) selecting a plurality of biomarkers; (b) selecting a means for determining the biomarker measures of said plurality of biomarkers; and (c) designing a system comprising said means for determining the biomarker measures and means for analyzing the biomarker measures to determine the likelihood that a subject is suffering from non-small cell lung cancer. Additionally, the biomarker measures described herein may avoid indication of asthma, breast cancer, prostate cancer, pancreatic cancer, or a combination thereof.

The invention also provides a method for designing a system for diagnosing non-small cell lung cancer in a subject comprising (a) selecting a plurality of biomarkers; (b) selecting a means for determining biomarker measures of said plurality of biomarkers; and (c) designing a system comprising said means for determining the biomarker measures and means for analyzing the biomarker measures to determine the likelihood that a subject is suffering from non-small cell lung cancer.

In the above methods, steps (b) and (c) may alternatively be performed by (b) selecting detection agents for detecting said plurality of biomarkers, and (c) designing a system comprising said detection agents for detecting plurality of biomarkers.

F. Male Population

The invention also provides a method for designing a system for assisting in diagnosing a lung disease in a male subject. Methods for these embodiments are similar to those described above.

G. Female Population

The invention also provides a method for designing a system for assisting in diagnosing a lung disease in a female subject. Methods for these embodiments are similar to those described above.

Classification Systems

The invention provides for systems that assist in performing the methods of the invention. The exemplary classification system comprises a storage device for storing a training data set and/or a test data set and a computer for executing a learning machine, such as a classifier or an ensemble of classifiers as described herein. The computer may also be operable for collecting the training data set from the database, pre-processing the training data set, training the learning machine using the pre-processed test data set and in response to receiving the test output of the trained learning machine, post-processing the test output to determine if the test output is an optimal solution. Such pre-processing may comprise, for example, visually inspecting the data to detect and remove obviously erroneous entries, normalizing the data by dividing by appropriate standard quantities, and ensuring that the data is in proper form for use in the respective algorithm. The exemplary system may also comprise a communications device for receiving the test data set and the training data set from a remote source. In such a case, the computer may be operable to store the training data set in the storage device prior to the pre-processing of the training data set and to store the test data set in the storage device prior to the pre-processing of the test data set. The exemplary system may also comprise a display device for displaying the post-processed test data. The computer of the exemplary system may further be operable for performing each additional function described above.

As used herein, the term "computer" is to be understood to include at least one hardware processor that uses at least one memory. The at least one memory may store a set of instructions. The instructions may be either permanently or temporarily stored in the memory or memories of the computer. The processor executes the instructions that are stored in the memory or memories in order to process data. The set of instructions may include various instructions that perform a particular task or tasks, such as those tasks described herein. Such a set of instructions for performing a particular task may be characterized as a program, software program, or simply software.

As noted above, the computer executes the instructions that are stored in the memory or memories to process data. This processing of data may be in response to commands by a user or users of the computer, in response to previous processing, in response to a request by another computer and/or any other input, for example.

The computer used to at least partially implement embodiments may be a general purpose computer. However, the computer may also utilize any of a wide variety of other technologies including a special purpose computer, a computer system including a microcomputer, mini-computer or mainframe for example, a programmed microprocessor, a micro-controller, a peripheral integrated circuit element, a CSIC (Customer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing at least some of the steps of the processes of the invention.

It is appreciated that in order to practice the method of the invention, it is not necessary that the processors and/or the memories of the computer be physically located in the same geographical place. That is, each of the processors and the memories used by the computer may be located in geographically distinct locations and connected so as to communicate in any suitable manner. Additionally, it is appreciated that each of the processor and/or the memory may be composed of different physical pieces of equipment.

Accordingly, it is not necessary that the processor be one single piece of equipment in one location and that the memory be another single piece of equipment in another location. That is, it is contemplated, for example, that the processor may be two or more pieces of equipment in two different physical locations. The two or more distinct pieces of equipment may be connected in any suitable manner, such as a network. Additionally, the memory may include two or more portions of memory in two or more physical locations.

Various technologies may be used to provide communication between the various computers, processors and/or memories, as well as to allow the processors and/or the memories of the invention to communicate with any other entity; e.g., so as to obtain further instructions or to access and use remote memory stores, for example. Such technologies used to provide such communication might include a network, the Internet, Intranet, Extranet, LAN, an Ethernet, or any client server system that provides communication, for example. Such communications technologies may use any suitable protocol such as TCP/IP, UDP, or OSI, for example.

Further, it is appreciated that the computer instructions or set of instructions used in the implementation and operation of the invention are in a suitable form such that a computer may read the instructions.

In some embodiments, a variety of user interfaces may be utilized to allow a human user to interface with the computer or machines that are used to at least partially implement the embodiment. A user interface may be in the form of a dialogue screen. A user interface may also include any of a mouse, touch screen, keyboard, voice reader, voice recognizer, dialogue screen, menu box, list, checkbox, toggle switch, a pushbutton or any other device that allows a user to receive information regarding the operation of the computer as it processes a set of instructions and/or provide the computer with information. Accordingly, a user interface is any device that provides communication between a user and a computer. The information provided by the user to the computer through the user interface may be in the form of a command, a selection of data, or some other input, for example.

It is also contemplated that a user interface of the invention might interact, e.g., convey and receive information, with another computer, rather than a human user. Accordingly, the other computer might be characterized as a user. Further, it is contemplated that a user interface utilized in the system and method of the invention may interact partially with another computer or computers, while also interacting partially with a human user.

The following examples are provided to exemplify various modes of the invention disclosed herein, but they are not intended to limit the invention in any way.

EXAMPLES

Example 1

Selection of Algorithm to Detect Non-Small Cell Lung Cancer

Example 1 illustrates the development and assessment of the different algorithms.

Selection of Biomarkers

This Example describes a procedure used to screen a set of 82 biomarkers to identify a subset of biomarkers that would be useful in a diagnostic method for non-small cell lung cancer which employs nonlinear classifiers to determine whether a patient is likely to suffer from the disease. The set of 82 biomarkers subjected to screening was based on results from prior studies plus 10-15 additional biomarkers that have been reported to have diagnostic potential for early stage lung cancer. The 82 biomarkers are bNGF, CA-125, CEA, CYFRA21-1, EGFR/HER1/ErBB1, GM-CSF, Granzyme B, Gro-alpha, ErbB2/HER2, HGF, IFN-a2, IFN-b, IFN-g, IL-10, IL-12p40, IL-12p70, IL-13, IL-15, IL-16, IL-17A, IL-17F, IL-1a, IL-1b, IL-1ra, IL-2, IL-20, IL-21, IL-22, IL-23p19, IL-27, IL-2ra, IL-3, IL-31, IL-4, IL-5, IL-6, IL-7, IL-8, IL-9, IP-10, I-TAC, Leptin, LIF, MCP-1, MCP-3, M-CSF, MIF, MIG, MIP-1a, MIP-1b, MIP-3a, MMP-7, MMP9, MPO, NSE, OPG, PAI-1, PDGF-AB/BB, PDGF, RANTES, Resistin, SAA, sCD40-ligand, SCF, SDF-1, SE-selectin, sFas ligand, sICAM-1, RANKL, TNFRI, TNFRII, sVCAM-1, TGF-α, TGF-β, TNF-α, TNF-β, TPO, TRAIL, TSP1, TSP2, VEGF-A, and VEGF-C.

Development of an algorithm as shown in this Example used 33 biomarkers selected from the set of 82 by the process illustrated in Example 2. Using a combination of biological subject matter expertise and statistical importance (see Table 6 for the importance of each biomarker as measured by the mean decrease in GINI) in the Random Forest model, 33 biomarkers were selected to be used for diagnostic determination of NSCLC. Literature and physio-clinical pathway search showed the majority of the selected biomarkers to have direct biological correlation or to be within the physio-clinical pathway with Lung Cancer, specifically NSCLC. The following biomarkers were used for analysis in the final algorithm development: IL-4, sEGFR, Leptin, NSE, MCP-1, GRO-pan, IL-10, IL-12P70, sCD40L, IL-7, IL-9, IL-2, IL-5, IL-8, IL-16, LIF, CXCL9/MIG, HGF, MIF, MMP-7, MMP-9, sFasL, CYFRA21-1, CA125, CEA, sICAM-1, MPO, RANTES, PDGF-AB/BB, Resistin, SAA, TNFRI, and sTNFRII. Race was not an important factor, and gender was only marginally important in discriminating NSCLC from other pathologies.

Study Population Criteria

The following inclusion criteria in Table 1 below were used for selecting subjects in the study population for this study.

TABLE 1

Inclusion Criteria for Selecting NSCLS and Control Population Samples.

| Samples | Gender | Age | Ethnicity | Cancer Stage | Smoking Status |
|---|---|---|---|---|---|
| NSCLC | M/F | NA | African American, | IA, IB, IIA, and IIB | Non-Smoker, Smoker |
| Healthy[4] | M/F | ≥45 y/o | Caucasian, or | Non NSCLC/NA | Non-Smoker |
| High Risk[5] | M/F | ≥45 y/o | Hispanic | Non NSCLC/NA | Smoker |

TABLE 1-continued

Inclusion Criteria for Selecting NSCLS and Control Population Samples.

| Samples | Gender | Age | Ethnicity | Cancer Stage | Smoking Status |
|---|---|---|---|---|---|
| Asthma | M/F | NA | | Non NSCLC/NA | Non-Smoker, Smoker |
| Other Cancer | M/F | NA | | All Stages | Non-Smoker, Smoker |

[4]Non-NSCLC, Non-Smoker, ≥45 y/o
[5]Non-NSCLC, Smoker, ≥45 y/o, Smoked 1 pack/day for 10 years Sample Size Selection The study sample size was determined as necessary to test the hypotheses:
$H_0$: Se<0.8 or Sp<0.8
$H_1$: Se>0.8 and Sp>0.8
where Se was the sensitivity of the Algorithm (equal to 1 minus the false positive rate) and Sp was the specificity of the Algorithm (equal to 1 minus the false negative rate). Given a Type I error of 0.05 and a Type II error of 0.2, 83 subjects were needed in each of the NSCLC and non-NSCLC cohort of the Validation Set (Table 2). The sample size of the Training Set was determined by past experience fitting SVMs and AdaBoost models on multiplex immunoassay data.

Study Samples

Samples from a total of 1,000 Subjects were run in duplicates yielding N=2,000 measurements for the Training and Validation Sets. From the 1,000 Subjects, a total of 554 Subjects (N=1,108) were randomized to a Training Set, and a total of 446 Subjects (N=892) were randomized to a blinded Validation Set to evaluate the performance of the algorithms. The algorithm developers were blinded to the pathology of the samples in the Validation Set. All samples were randomized to either the Training Set or Validation Set, to the plate on which they were analyzed, and to the location on the plate. Cohorts were distributed evenly across the total plates of the study. Samples consist of a mixture of African-American, Caucasian, and Hispanic population. Table 2 shows how various cohorts are distributed between Training and Validation Sets.

TABLE 2

Sample Size by Disease, Smoking Status, and Gender.

| Cohort | Training Set | Validation Set | Total |
|---|---|---|---|
| NSCLC | 160 | 119 | 280 |
| Asthma | 33 | 32 | 65 |
| Smoker | 131 | 110 | 241 |
| Non-Smoker | 140 | 130 | 270 |
| Other Cancer[6] | 90 | 55 | 144 |
| Total | 554 | 446 | 1000 |

[6]Other Cancers include Breast, Ovarian, Prostate, Pancreatic, and Colon-Rectal Cancer Sample Procurement, Handling, and Storage Human plasma samples, collected in disodium EDTA tubes ($Na_2$-EDTA) were used. Blood samples were stored on ice for up to an hour after collection and centrifuged for 10 minutes at 1500×g at 4° C./39° F. The plasma is then transferred to a 15 ml conical tube and re-centrifuged. The plasma samples were stored in single-use aliquots at −80° C. to avoid multiple freeze-thaw cycles. Plasma samples prepared by this procedure were obtained from Asterand, BioReclammation, BioSource, Geneticist, and Proteogenex.

Control Handling Procedure

Millipore Quality Control 1 and Quality Control 2 were developed in lyophilized format and stored at 2-8° C. Each control vial was reconstituted with 100 µL deionized water, inverted several times, vortexed, and incubated for 5-10 minutes on ice. Unused portion was stored at ≤−20° C. for up to one month.

Equipment and Conditions

Data were collected using the FLEXMAP 3D Luminex instrument. The Integra ViaFlo 96 robot was used for sample and reagent transfers in the plates.

Test Methodology

Biomarker measures for the various biomarkers in physiological samples were obtained by assays designed on magnetic beads using a capture sandwich immunoassay format. The capture antibody-coupled beads were incubated overnight with assay buffer, serum/plasma matrix solution and antigen standards, samples, blanks, or controls. Overnight incubations (16-18 hours) were done at 2-8° C. on a plate shaker at 500-800 rpm. The next day, the beads were washed 2 times. All washes and reagent transfers were done using a semi-automated process by ViaFlo96 from Integra. All next day incubations done were at room temperature (20-25° C.) at 500-800 rpm. After the wash, the detection antibodies were added and incubated for 60 minutes. Then the beads were incubated with a reporter Streptavidin-Phycoerythrin conjugate (SA-PE) for 30 minutes. The beads were washed 2 times to remove excess detection antibody and SA-PE. Sheath fluid was added to the beads and placed on the shaker for 5 minutes. The plate was read using the FlexMap 3D, which measures the fluorescence of the beads and of the bound SA-PE. The data was acquired using the Exponent software and then imported into the Bio-Plex Manager 6.1 for data analysis at low PMT setting.

Computerized Systems and Software

Data collection was performed using the Luminex xPONENT acquisition software. Data from the Bio-Rad Bio-Plex Manager™ 6.1 Standard Edition Software was used for the analysis.

Parameters for Data Analysis

The parameters below were applied for the data analysis process. The acceptance criteria below were in compliance with the FDA Guidance for the Industry: Bioanalytical Method Validation [2013].

The following assay acceptance criteria were applied to all the plate runs and for each individual biomarker for all assay wells. The same rules were applied for the Standard/Calibration Curve, Samples, and Controls.

1) Dose Recovery Range 100±20% (80%-120%)
2) Regression Type Logistic 5PL (Nonlinear)
3) Minimum of 6 Standard Points required
4) Background MFI<200
5) Bead Count≥50

6) Intra-assay<15% using Conc In Range and FI values (≤20% for values at LLOQ)
7) Inter-assay<20% using Conc In Range and FI values (≤25% for values at LLOQ)
8) Outliers for sample data were not removed due to inability to detect outliers in duplicates Concentration Analysis Methods Multiplex immunoassay standard curves were nonlinear and concentration-response relationship were fitted to a 5-parameter logistic model for this study. This regression method required a minimum of 6 standard points. The Standard Curves were calculated using the Logistic-5PL regression method using the Bio-Plex Manager Software 6.1. The 5-PL Logistic Calculation was:

$Y = d + (a-d)/[1+(x/c)^b]^g$ where:

x is the concentration
y is the response
a is the estimate response at infinite concentration
b is the slope of the tangent at midpoint
c is the midrange concentration or midpoint
d is the estimated response at zero concentration
g is an asymmetry factor The precision of the assay was assessed by determining the coefficient of variation (CV) from the average and standard deviation (SD) of all runs, % CV=(SD/Mean) and expressed as a percentage.

Recovery was calculated using the following formula: R=(Observed Value/Expected Value)×100%. The Observed Value (OV), also known as the Observed Concentration, was the measured value of an analyte that was quantitated and reported in pg/mL. The Expected Value (EV), also known as the Expected Concentration, was the value in pg/mL of an analyte that was expected to be measured for a dilution using a standard antigen.

Algorithm Method Analysis
Algorithm Model Development

This Example tested six (6) different algorithm forms for selection of the Algorithm model. The Data Analysis considered duplicate measurements of 33 biomarkers in a physiological sample from a subject, as well as the subject's gender and smoking status, and classified each measurement as having NSCLC or not. The Algorithm models were developed on the training set. Once the algorithm was fully trained, its performance was analyzed on the blinded validation set. The final Algorithm model was selected from the best performing of the following algorithms (or a combination thereof):

(1) Genetic Algorithm—SVM
(2) Random Forest
(3) LASSO
(4) Ridge Regression
(5) AdaBoost as determined by their sensitivity and specificity under 10-fold cross validation.

Of the above models, the Random Forest model had the best performance. Therefore Random Forest is used as the classifier algorithm in subsequent analyses of the biomarker measures according to this invention [Table 3]. The analytical model according to this Example has a sensitivity of 0.982 (95% CI: 0.921-0.998) and a specificity of 0.865 (95% CI: 0.802-0.914). When removing other cancers besides NSCLC from the data set, the specificity increases to 0.967 (95% CI: 0.916-0.991). Each subject was assigned to one set: (1) the training set, on which the model was constructed, or (2) the validation set, on which model performance was measured.

TABLE 3

10-Fold Cross-Validation for the 6 Multivariate Classification Algorithm Using 33 Biomarkers.

|  | Accuracy (CI) | Sensitivity (CI) | Specificity (CI) | PPV (CI) | NPV (CI) |
| --- | --- | --- | --- | --- | --- |
| RF | 0.899 | 0.982 | 0.865 | 0.747 | 0.992 |
|  | (0.851-0.935) | (0.921-0.998) | (0.802-0.914) | (0.640-0.835) | (0.963-0.999) |
| AdaBoost | 0.884 | 0.947 | 0.858 | 0.73 | 0.956 |
|  | (0.834-0.923) | (0.866-0.985) | (0.794-0.901) | (0.621-0.821) | (0.937-0.993) |
| Lasso | 0.869 | 0.912 | 0.851 | 0.712 | 0.96 |
|  | (0.816-0.910) | (0.818-0.968) | (0.785-0.902) | (0.602-0.806) | (0.915-0.985) |
| RR | 0.869 | 0.895 | 0.858 | 0.718 | 0.956 |
|  | (0.816-0.910) | (0.796-0.955) | (0.794-0.901) | (0.607-0.813) | (0.937-0.993) |
| GA | 0.798 | 0.79 | 0.801 | 0.616 | 0.904 |
|  | (0.738-0.849) | (0.671-0.879) | (0.730-0.861) | (0.502-0.723) | (0.843-0.946) |
| SVM | 0.864 | 0.877 | 0.858 | 0.714 | 0.945 |
|  | (0.811-0.906) | (0.774-0.943) | (0.794-0.901) | (0.601-0.810) | (0.896-0.975) |

NPV, Negative Predictive Value;
PPV, Positive Predictive Value;
CI, 95% Confidence Interval;
SVM, Support Vector Machine;
RF, Random Forest;
RR, Ridge Regression;
GA, Genetic Algorithms.

Example 1a

Review of Algorithms for NSCLC Detection

Example 1a furthers the selection of the final algorithm by reviewing additional algorithms: elastic nets, gradient tree boosting, k-nearest neighbors, and Bayesian neural networks.

The following biomarkers were used for analysis in the final algorithm development: IL-4, sEGFR, Leptin, NSE, MCP-1, GRO-pan, IL-10, IL-12P70, sCD40L, IL-7, IL-9, IL-2, IL-5, IL-8, IL-16, LIF, CXCL9/MIG, HGF, MIF, MMP-7, MMP-9, sFasL, CYFRA21-1, CA125, CEA, sICAM-1, MPO, RANTES, PDGF-AB/BB, Resistin, SAA, TNFRI, and sTNFRII. Race was not an important factor, and gender was only marginally important in discriminating NSCLC from other pathologies.

Study Samples

The study samples for Example 1a are as described in Example 1.

Study Population Criteria

The inclusion criteria of Example 1 were used for selecting the study population samples this study.

Sample Size Selection

Sample size selection criteria were the same as the criteria used for Example 1.

Procedures and Equipment

Sample procurement, handling and storage were the same as those used for Example 1.

Test Methodology

The Screening Assays were performed as described in Example 1.

Algorithm Model Evaluation

This Example tested a further six (6) different algorithm forms to compare against the Random Forest model selected from Example 1. The Data Analysis considered duplicate measurements of 33 biomarkers in a physiological sample from a subject, as well as the subject's gender and smoking status, and classified each measurement as having NSCLC or not. The Algorithm models were developed on the training set. Once the algorithm was fully trained, its performance was analyzed on the blinded validation set. The algorithm models examined (or a combination thereof) are:

Elastic Nets
Gradient Boosting Trees
Neural Network
Bayesian Neural Network
k-Nearest Neighbor
Naïve Bayes None of the additional models beat the model fit using the Random Forest algorithm. In the case of the neural network based algorithms, the models may not have had sufficient data to fit the model well. However, the addition of more data should improve the model fit.

Example 2

Selection of Subgroup of Biomarkers

Example 2 exemplifies the selection of the 33 biomarkers using Random Forest as the classification algorithm.

Selection of Biomarkers

In this study, 33 biomarkers were selected to have diagnostic potential for early stage lung cancer. The 33 biomarkers are CA-125, CEA, CYFRA21-1, EGFR/HER1/ErBB1, Gro-Pan, HGF, IL-10, IL-12p70, IL-16, IL-2, IL-4, IL-5, IL-7, IL-8, IL-9, Leptin, LIF, MCP-1, MIF, MIG, MMP9, MPO, NSE, PDGF-AB/BB, RANTES, Resistin, sFasL, SAA, sCD40-ligand, sICAM-1, TNFRI, and TNFRII.

Algorithm

The Algorithm model for the classifier considers duplicate measurements of 33 biomarkers from a subject, as well as their gender and smoking status, and classifies each measurement by disease state. Using the Random Forest algorithm, each of the duplicate measurements for a subject was classified as having NSCLC or not having NSCLC. If any of the measurements were classified as being from a subject with NSCLC, the subject was classified as having NSCLC. This algorithm tends to err on the side of predicting that a subject has NSCLC. This is due to the inherent costs of allowing the disease to progress without treatment.

Study Samples

A total of 1,258 Subjects (2,516 samples) were processed in duplicates yielding N=2,514 measurements. All samples were randomized, and cohorts were distributed evenly across the total plates of the study.

Study Population Criteria

The inclusion criteria of Example 1 were used for selecting the study population samples this study.

Sample Size Selection

Sample size selection criteria were the same as the criteria used for Example 1. The sample cohorts for this study are described in Table 4.

TABLE 4

10-Fold Cross-Validation for the 6 Additional Multivariate Classification Algorithm Using 33 Biomarkers.

|     | Accuracy (CI) | Sensitivity (CI) | Specificity (CI) | PPV (CI) | NPV (CI) |
| --- | --- | --- | --- | --- | --- |
| EN  | 0.879 | 0.930 | 0.858 | 0.726 | 0.968 |
|     | (0.828-0.919) | (0.842-0.976) | (0.794-0.901) | (0.616-0.818) | (0.926-0.989) |
| GBT | 0.869 | 0.912 | 0.851 | 0.712 | 0.96 |
|     | (0.816-0.910) | (0.818-0.968) | (0.785-0.902) | (0.602-0.806) | (0.915-0.985) |
| NN  | 0.798 | 0.842 | 0.780 | 0.608 | 0.924 |
|     | (0.738-0.849) | (0.732-0.919) | (0.707-0.842) | (0.498-0.710) | (0.867-0.962) |
| BNN | 0.798 | 0.842 | 0.780 | 0.608 | 0.924 |
|     | (0.738-0.849) | (0.732-0.919) | (0.707-0.842) | (0.498-0.710) | (0.867-0.962) |
| kNN | 0.833 | 0.895 | 0.809 | 0.654 | 0.95 |
|     | (0.777-0.880) | (0.796-0.955) | (0.738-0.867) | (0.544-0.752) | (0.900-0.979) |
| NB  | 0.843 | 0.877 | 0.830 | 0.676 | 0.944 |
|     | (0.788-0.889) | (0.774-0.943) | (0.761-0.885) | (0.564-0.774) | (0.892-0.974) |

NPV, Negative Predictive Value;
PPV, Positive Predictive Value;
CI, 95% Confidence Interval;
EN: Elastic Nets;
GBT: Gradient Boosting Trees;
NN: Neural Network;
BNN: Bayesian Neural Network;
kNN: k-Nearest Neighbor;
NB: Naïve Bayes

TABLE 4

Sample Size by Disease, Smoking Status, and Gender

| Pathology | Total (N) | Female (N) | Male (N) |
|---|---|---|---|
| Asthma | 134 | 98 | 36 |
| Breast Cancer | 100 | 100 | |
| CRC | 166 | 89 | 77 |
| Non-Smoker | 180 | 90 | 90 |
| NSCLC | 245 | 101 | 144 |
| Ovarian Cancer | 90 | 90 | |
| Pancreatic Cancer | 62 | 33 | 29 |
| Prostate Cancer | 98 | | 98 |
| Smoker | 183 | 90 | 93 |
| Grand Total | 1258 | 691 | 567 |

Procedures and Equipment

Sample procurement, handling and storage were the same as those used for Example 1.

Test Methodology

The Screening Assays were performed as described in Example 1.

Algorithm Model Evaluation

The Algorithm was constructed using a Random Forest model in this study. This model has a sensitivity of 0.982 (95% CI: 0.921-0.998) and specificity of 0.865 (95% CI: 0.802-0.914) for NSCLC. The specificity of the algorithm increases to 0.967 (95% CI: 0.916-0.991) when the non-NSCLC cancers are removed from the data set.

Biomarker Selection Using the Algorithm

After the Algorithm is evaluated, 9-33 biomarkers indicative for NSCLC can be used as components for a diagnostic kit. This selection may be based on the variable importance statistic, or the number of iterations of the algorithm and location in the CART that a particular biomarker appears in, as well as biological relevance.

Clinical Accuracy

Diagnostic Accuracy Using Clinical Reference

Diagnostic accuracy was calculated as the number of subjects with NSCLC who are predicted to have NSCLC plus the number of subjects without NSCLC and were predicted not to have NSCLC divided by the total number of subjects. Sample pathology was determined by a Medical Pathologist as reported by the sample providers.

The performance of the diagnostic test may be expressed as the positive predictive value (PPV) and negative predictive value (NPV). Positive predictive value (PPV) is the number of true positives (TP) divided by the number of true positives (TP) plus the number of false positives (FP), PPV=TP/(TP+FP). Negative predictive value (NPV) is the number of true negatives (TN) divided by the number of true negatives (TN) plus the number of false negatives (FP), NPV=TN/(TN+FN).

Sensitivity is defined as the probability of a positive result for a patient with NSCLC. Sensitivity is calculated as the number of true positives (TP) divided by total number of actual NSCLC patients, or number of true positives (TP) plus the number of false negatives (FN); Sensitivity=TP/(TP+FN).

Specificity is defined as the probability that the patient does not have NSCLC. Specificity is calculated as the number of true negatives (TN) divided by total number of actual Non-NSCLC patients, or number of true negatives (TN) plus the number of false positives (FP); Specificity=TN/(TN+FP).

Specificity

Clinical specificity of the test is a measure of the ability of the algorithm to correctly identify those patients without the disease of interest. To demonstrate that the Test of this invention is specific for NSCLC, a total of 144 samples (N=288) from other types of cancers, other than NSCLC, were tested. 90 of these non-NSCLC cancers were included in the Training Set. The following cancers were included:

(1) Breast Cancer (26F)
(2) Colon-Rectal Cancer (26F, 22M)
(3) Ovarian Cancer (25F)
(4) Pancreatic Cancer (15F, 15M)
(5) Prostate Cancer (15M)

The algorithm classified the samples as belonging to patients with NSCLC or not; the test result does not take into account if another type of cancer is present. To determine cross-reactivity of other cancers with NSCLC, the error rate for each specific cancers was examined.

The Algorithm can classify samples as belong to patients with NSCLC or not, without considering if they have another type of cancer. In order to determine the cross reactivity of other cancers with NSCLC, the False Positive Rate (FPR) for each specific cancer as well as the False Negative Rate (FNR) for all non-NSCLC cancers were examined.

TABLE 5

False Negative Rate Using the Algorithm.

| Actual | Positive | Negative | Pathology Error Rate | 95% CI | |
|---|---|---|---|---|---|
| Asthma | 11 | 3 | 21% | 6% | 47% |
| Breast Cancer | 5 | 3 | 38% | 12% | 71% |
| CRC | 9 | 6 | 40% | 19% | 65% |
| Non-Smoker | 32 | 6 | 16% | 7% | 30% |
| NSCLC | 56 | 1 | 2% | 0% | 8% |
| Ovarian Cancer | 5 | 2 | 29% | 6% | 65% |
| Pancreatic Cancer | 6 | 7 | 54% | 28% | 78% |
| Prostate Cancer | 4 | 2 | 33% | 8% | 71% |
| Smoker | 33 | 7 | 18% | 8% | 31% |

The algorithm has a false negative rate of 0.02 for NSCLC and a false positive rate of 0.13. This means that 2 out of 100 NSCLC patients will not be detected as having the disease and 13 out of 100 non-NSCLC patients will have a positive result for the disease.

The Algorithm can classify samples as belong to patients with NSCLC or not, without considering if they have another type of cancer. In order to determine the cross reactivity of other cancers with NSCLC, the False Positive Rate (FPR) for each specific cancer as well as the False Negative Rate (FNR) for all non-NSCLC cancers were examined.

Algorithm Model Evaluation Results

Algorithms for three sets of biomarkers (33, 19, and 13) were constructed using a Random Forest model with the samples from US subjects. The results for the training set for these algorithms are shown on Table 6. The first model used 33 biomarkers and had a sensitivity of 0.928 (CI: 0.879, 0.961) and specificity of 0.972 (CI: 0.955, 0.988) for NSCLC. The second model used 19 biomarkers and had a sensitivity of 0.924 (CI: 0.892, 0.943) and specificity of 0.969 (CI: 0.952, 0.980) for NSCLC. The third model used 13 biomarkers and had a sensitivity of 0.890 (CI: 0.861, 0.918) and specificity of 0.958 (CI: 0.941, 0.972) for NSCLC.

TABLE 6

List of Biomarkers and Algorithm Model Size.

| Biomarker | Importance | Algorithm 33 | Algorithm 19 | Algorithm 13 |
|---|---|---|---|---|
| IL-8 | 65.99 | X | X | X |
| MMP-9 | 47.21 | X | X | X |
| sTNFRII | 34.5 | X | X | X |
| TNFRI | 23.96 | X | X | X |
| MMP-7 | 4.81 | X | X | |
| IL-5 | 3.5 | X | X | |
| Resistin | 3.41 | X | X | X |
| IL-10 | 3.27 | X | X | |
| MPO | 2.55 | X | X | X |
| NSE | 2.51 | X | X | X |
| MCP-1 | 2.43 | X | X | |
| GRO-Pan | 2.21 | X | X | X |
| CEA | 2.18 | X | X | X |
| Leptin | 1.78 | X | X | |
| CXCL9/MIG | 1.66 | X | X | X |
| HGF | 1.2 | X | | |
| sCD40L | 1.08 | X | | |
| CYFRA 21-1 | 0.92 | X | X | |
| sFasL | 0.72 | X | | |
| RANTES | 0.71 | X | | |
| IL-7 | 0.7 | X | | |
| MIF | 0.67 | X | X | |
| sICAM-1 | 0.63 | X | X | |
| IL-2 | 0.61 | X | | X |
| SAA | 0.56 | X | X | X |
| 1L-16 | 0.56 | X | | |
| IL-9 | 0.51 | X | | |
| PDGF-AB/BB | 0.5 | X | | X |
| sEGFR | 0.5 | X | | |
| LIF | 0.49 | X | | |
| IL.12p70 | 0.47 | X | | |
| CA125 | 0.42 | X | | |
| IL-4 | 0.11 | X | | |
| #Biomarkers | | 33 | 19 | 13 |
| SE (Training) | | 0.928 (CI: 0.879, 0.961) | 0.924 (CI: 0.892, 0.943) | 0.890 (CI: 0.861, 0.918) |
| SP (Training) | | 0.972 (CI: 0.955, 0.988) | 0.969 (CI: 0.952, 0.980) | 0.958 (CI: 0.941, 0.972) |

Example 3

Validating the Performance of the Final Algorithm Models Restricted to the US Population This Example presents the results of the blind study using the 33 selected biomarkers and algorithms with 33, 19 and 13 biomarkers as developed in Example 1 and 2.

For this Example, samples were processed using the same reagents and methods used in Examples 1 and 2. A total of 228 Subjects were processed in duplicates, yielding 456 measurements (Table 7). Samples consisted of African-Americans, Caucasians, and Hispanics, and originated from the United States (Table 8). Samples were blinded and randomized with the cohorts distributed evenly across the total plates of the study.

TABLE 7

Sample Size by Pathology, Gender, and Age.

| Pathology | Total (n) | Female (n) | Male (n) | Age Range |
|---|---|---|---|---|
| Asthma | 11 | 8 | 3 | 38-67 |
| Breast Cancer | 40 | 40 | 0 | 35-92 |
| CRC | 5 | 3 | 2 | 44-91 |
| Non-Smoker | 57 | 30 | 27 | 45-85 |
| NSCLC* | 55 | 27 | 28 | 48-91 |
| Pancreatic Cancer | 3 | 2 | 1 | 49-82 |

TABLE 7-continued

Sample Size by Pathology, Gender, and Age.

| Pathology | Total (n) | Female (n) | Male (n) | Age Range |
|---|---|---|---|---|
| Prostate | 9 | 0 | 9 | 45-73 |
| Smoker | 48 | 25 | 23 | 40-70 |
| Grand Total | 228 | 135 | 93 | 35-92 |

*All NSCLC samples were Stage I.

TABLE 8

Sample Distribution by Gender, Pathology and Race.

| Cohort | African-American | Caucasian | Hispanic | Total |
|---|---|---|---|---|
| Female | 29 | 88 | 18 | 135 |
| Asthma | 0 | 8 | 0 | 8 |
| Breast Cancer | 5 | 35 | 0 | 40 |
| CRC | 0 | 3 | 0 | 3 |
| Non-Smoker | 9 | 12 | 9 | 30 |
| NSCLC | 6 | 17 | 4 | 27 |
| Pancreatic Cancer | 0 | 2 | 0 | 2 |
| Smoker | 9 | 11 | 5 | 25 |
| Male | 25 | 51 | 17 | 93 |
| Asthma | 0 | 3 | 0 | 3 |
| CRC | 0 | 2 | 0 | 2 |
| Non-Smoker | 7 | 11 | 9 | 27 |
| NSCLC | 5 | 18 | 5 | 29 |
| Pancreatic Cancer | 0 | 1 | 0 | 1 |
| Prostate | 3 | 6 | 0 | 9 |
| Smoker | 10 | 10 | 3 | 23 |
| Total | 54 | 139 | 35 | 228 |

*All samples originated from the United States

Algorithm Model Evaluation

The three different sized algorithms constructed using a Random Forest model developed in Example 2 for different numbers of biomarkers (33, 19, and 13), were tested against validation samples from US subjects (Table 9). Data from the 228 subjects was blinded and used to validate the performance of the algorithms of this invention using 33, 19, and 13 biomarkers. After the results were tallied, the pathology was released, and the set was used for retraining of the algorithm. All data points obtained from each subject were utilized in the evaluation of the algorithm performance. Because the underlying distribution of the concentrations of the biomarkers can be assumed to be log-normal, values censored below the LLOQ can be estimated by the LLOQ divided by the square root of two. Similarly, values censored above the ULOQ can be estimated by the ULOQ multiplied by the square root of two. Thus, all subjects were included in the analysis.

TABLE 9

Blind Set Performance.

| Statistic (95% CI) | Algorithm 33 | Algorithm 19 | Algorithm 13 |
|---|---|---|---|
| Accuracy | 0.956 | 0.956 | 0.934 |
|  | (0.924, 0.977) | (0.924, 0.977) | (0.896, 0.961) |
| Sensitivity | 0.891 | 0.891 | 0.873 |
|  | (0.789, 0.953) | (0.789, 0.953) | (0.766, 0.941) |
| Specificity | 0.977 | 0.977 | 0.954 |
|  | (0.946, 0.992) | (0.946, 0.992) | (0.915, 0.978) |

Estimate (LCL, UCL)

Clinical Parameters and Results

In the clinical setting, the PPV and NPV are more useful in determining the value of a test since these measures are indicative of the prevalence of the disease in the population of interest. A highly sensitive test is important where the test is used to identify a serious but treatable disease, and a highly specific test avoids further subjection of the patient to further unnecessary follow-up medical procedures. The summarized results of the blind test can be found in Table 10. The blind set sample consisted of 228 subjects (N=456) distributed into the following: 11 asthma, 40 breast cancer, 5 colorectal cancer, 57 non-smokers, 55 Stage I NSCLC, 3 pancreatic cancers, 9 prostate cancers, and 48 smokers.

TABLE 10

Prevalence, PPV, NPV, TP, TN, FP and FN.

| Statistics | Model USA (33) | Model USA (19) | Model USA (13) |
|---|---|---|---|
| Accuracy | 0.956 | 0.956 | 0.934 |
|  | (0.924, 0.977) | (0.924, 0.977) | (0.896, 0.961) |
| True Positive Rate (TPR) | 0.891 | 0.891 | 0.873 |
|  | (0.789, 0.953) | (0.789, 0.953) | (0.766, 0.941) |
| False Positive Rate (FPR) | 0.023 | 0.023 | 0.046 |
|  | (0.008, 0.054) | (0.008, 0.054) | (0.022, 0.085) |
| Sensitivity | 0.891 | 0.891 | 0.873 |
|  | (0.789, 0.953) | (0.789, 0.953) | (0.766, 0.941) |
| Specificity | 0.977 | 0.977 | 0.954 |
|  | (0.946, 0.992) | (0.946, 0.992) | (0.915, 0.978) |
| Positive Predictive Value (PPV) | 0.925 | 0.925 | 0.857 |
|  | (0.830, 0.974) | (0.830, 0.974) | (0.748, 0.930) |
| Negative Predictive Value (NPV) | 0.966 | 0.966 | 0.959 |
|  | (0.931, 0.986) | (0.931, 0.986) | (0.922, 0.982) |
| Prevalence | 0.241 | 0.241 | 0.241 |
| True Positive (TP) | 49 | 49 | 48 |
| True Negative (TN) | 169 | 169 | 165 |
| False Positive (FP) | 4 | 4 | 8 |
| False Negative (FN) | 6 | 6 | 7 |

ROC by Biomarker

Figure 1B:
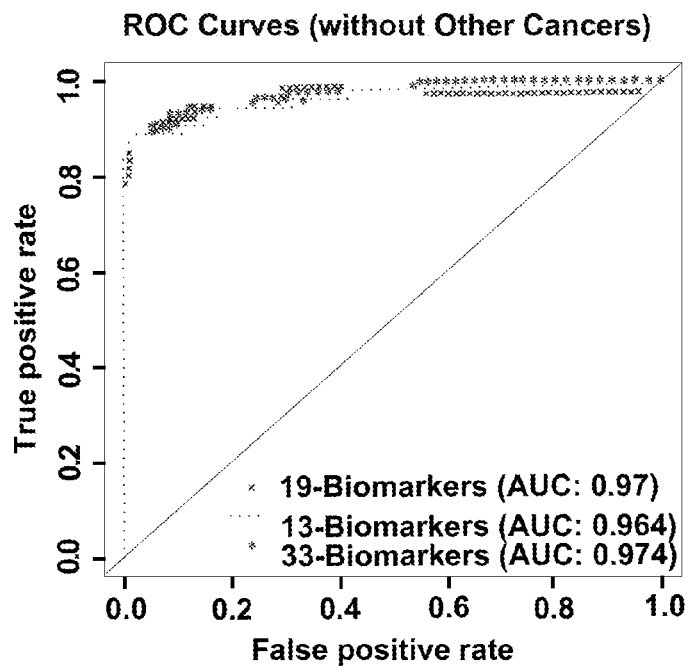

Receiver operator characteristic (ROC) curves plot the false positives rate (1—specificity) against the true positives rate (sensitivity) for all possible cut-off values of the classifier. FIGS. 1A & B shows the ROC curves for Random Forest models using 19 biomarkers and 13 biomarkers. The area under the curve (AUC) represents the area under the curve of the ROC curve. The AUC of a perfect test is 1.0 and that of a random guess is 0.5. In general, an AUC above 0.8 is sufficient, however, for our application, the target is an AUC of 0.9 or greater. Algorithms with 33, 19 and 13 biomarkers have an AUC of 0.963, 0.960, and 0.951, respectively. FIG. 1A-B illustrates the ROC Curves for the 33, 19 and 13 biomarkers. This indicates that the two models have good discriminatory ability between NSCLC and not-NSCLC. Furthermore, it indicates that AUC slightly improves when non-NSCLC cancers are excluded from the analyzed data.

Diagnostic Accuracy and Clinical Specificity

Clinical specificity of a test is a measure of the ability of the algorithm to correctly identify those patients without the disease of interest. To demonstrate that the Test according to this invention is specific for NSCLC, a total of 57 samples (N=114) from other types of cancers, other than NSCLC, were tested. The following cancers were included:
(1) Breast Cancer (40)
(2) Colon-Rectal Cancer (5)
(3) Pancreatic Cancer (3)
(4) Prostate Cancer (9)

The algorithm classified the samples as belonging to patients with NSCLC or not; the test result does not take into account if another type of cancer is present. In order to determine cross reactivity of other cancers with NSCLC, the error rate for each specific cancers was examined.

The test of this invention with 33, 19 and 13 biomarkers has an error rate of 10.91%, 10.91% and 12.73% for NSCLC, respectively. As an example, 6 out of 55 NSCLC subjects will not be detected as having NSCLC by the test according to this invention using the 33 or 19 biomarker model. The results are as follows:

TABLE 11

Actual and predicted results using algorithm with 33 biomarkers.

| | | Predicted Non-NSCLC | NSCLC | Total | Class Error |
|---|---|---|---|---|---|
| Actual | Asthma | 10 | 1 | 11 | 9.09% |
| | Breast | 37 | 3 | 40 | 7.50% |
| | CRC | 5 | 0 | 5 | 0.00% |
| | Non-Smoker | 57 | 0 | 57 | 0.00% |
| | NSCLC | 6 | 49 | 55 | 10.91% |
| | Pancreatic | 3 | 0 | 3 | 0.00% |
| | Prostate | 9 | 0 | 9 | 0.00% |
| | Smoker | 48 | 0 | 48 | 0.00% |
| | Total | 175 | 53 | 228 | |

LCL—Lower 95% confidence limit,
UCL—Upper 95% confidence limit

TABLE 12

Actual and predicted results using algorithm with 19 biomarkers.

| | | Predicted Non-NSCLC | NSCLC | Total | Class Error |
|---|---|---|---|---|---|
| Actual | Asthma | 10 | 1 | 11 | 9.09% |
| | Breast | 37 | 3 | 40 | 7.50% |
| | CRC | 5 | 0 | 5 | 0.00% |
| | Non-Smoker | 57 | 0 | 57 | 0.00% |
| | NSCLC | 6 | 49 | 55 | 10.91% |
| | Pancreatic | 3 | 0 | 3 | 0.00% |
| | Prostate | 9 | 0 | 9 | 0.00% |
| | Smoker | 48 | 0 | 48 | 0.00% |
| | Total | 175 | 53 | 228 | |

LCL—Lower 95% confidence limit,
UCL—Upper 95% confidence limit

TABLE 13

Actual and predicted results using algorithm with 13 biomarkers.

| | | Predicted Non-NSCLC | NSCLC | Total | Class Error |
|---|---|---|---|---|---|
| Actual | Asthma | 10 | 1 | 11 | 9.09% |
| | Breast | 34 | 6 | 40 | 15.00% |
| | CRC | 4 | 1 | 5 | 20.00% |
| | Non-Smoker | 57 | 0 | 57 | 0.00% |
| | NSCLC | 7 | 48 | 55 | 12.73% |
| | Pancreatic | 3 | 0 | 3 | 0.00% |
| | Prostate | 9 | 0 | 9 | 0.00% |
| | Smoker | 48 | 0 | 48 | 0.00% |
| | Total | 172 | 56 | 228 | |

LCL—Lower 95% confidence limit,
UCL—Upper 95% confidence limit

Table 14, 15 and 16 represents results when other non-NSCLC cancer samples were excluded from the dataset.

TABLE 14

Actual and predicted results using algorithm with 33 biomarkers and excluding other cancer samples.

| | | Predicted Non-NSCLC | NSCLC | Total | Class Error |
|---|---|---|---|---|---|
| Actual | Asthma | 10 | 1 | 11 | 9.09% |
| | Non-Smoker | 57 | 0 | 57 | 0.00% |
| | NSCLC | 6 | 49 | 55 | 10.91% |
| | Smoker | 48 | 0 | 48 | 0.00% |
| | Total | 121 | 50 | 171 | |

LCL—Lower 95% confidence limit,
UCL—Upper 95% confidence limit

TABLE 15

Actual and predicted results using algorithm with 19 biomarkers and excluding other cancer samples.

| | | Predicted Non-NSCLC | NSCLC | Total | Class Error |
|---|---|---|---|---|---|
| Actual | Asthma | 10 | 1 | 11 | 9.09% |
| | Non-Smoker | 57 | 0 | 57 | 0.00% |
| | NSCLC | 6 | 49 | 55 | 10.91% |
| | Smoker | 48 | 0 | 48 | 0.00% |
| | Total | 121 | 50 | 171 | |

LCL—Lower 95% confidence limit,
UCL—Upper 95% confidence limit

TABLE 16

Actual and predicted results using algorithm with 13 biomarkers and excluding other cancer samples.

| | | Predicted Non-NSCLC | NSCLC | Total | Class Error |
|---|---|---|---|---|---|
| Actual | Asthma | 10 | 1 | 11 | 9.09% |
| | Non-Smoker | 57 | 0 | 57 | 0.00% |
| | NSCLC | 7 | 48 | 55 | 12.73% |
| | Smoker | 48 | 0 | 48 | 0.00% |
| | Total | 122 | 49 | 171 | |

LCL—Lower confidence limit,
UCL—Upper confidence limit

Random Algorithm Sampling Using 21 Biomarkers

A final set of 21 biomarkers was selected based on results from Algorithms with 13 and 19 biomarkers. To test for robustness of these biomarkers, a combination between 10-21 biomarkers was randomly selected from the set of 21. That algorithm was run on the blinded set. The results on Table 19 indicate that this set of biomarkers are robust and provides flexibility in the number of biomarkers used for the algorithm. AUC was calculated for Algorithms with 21 biomarkers (0.964), 20 biomarkers (0.963), 19 biomarkers (0.966), and 13 biomarkers (0.955). The average statistics for the 20 random sampling using the 21 biomarkers are at 92% accuracy, 81% sensitivity, and 96% specificity.

TABLE 17

Random Algorithm Sampling Using the Final 21 CPC Biomarkers.

| Biomarkers | Accuracy | Sensitivity | Specificity | PPV | NPV | Prevalence |
|---|---|---|---|---|---|---|
| 10 | 0.939 | 0.873 | 0.960 | 0.873 | 0.960 | 0.241 |
| 11 | 0.934 | 0.857 | 0.959 | 0.873 | 0.954 | 0.241 |
| 12 | 0.934 | 0.857 | 0.959 | 0.873 | 0.954 | 0.241 |
| 13 | 0.930 | 0.842 | 0.959 | 0.873 | 0.948 | 0.241 |
| 14 | 0.930 | 0.842 | 0.959 | 0.873 | 0.948 | 0.241 |
| 15 | 0.939 | 0.860 | 0.965 | 0.891 | 0.954 | 0.241 |
| 16 | 0.934 | 0.857 | 0.959 | 0.873 | 0.954 | 0.241 |
| 17 | 0.939 | 0.902 | 0.949 | 0.836 | 0.971 | 0.241 |
| 18 | 0.947 | 0.939 | 0.950 | 0.836 | 0.983 | 0.241 |
| 19 | 0.961 | 0.960 | 0.961 | 0.873 | 0.988 | 0.241 |
| 20 | 0.917 | 0.790 | 0.964 | 0.891 | 0.925 | 0.241 |
| 21 | 0.921 | 0.803 | 0.964 | 0.891 | 0.931 | 0.241 |
| AUC < 0.8 | 0.842 | 0.623 | 0.954 | 0.873 | 0.832 | 0.241 |
| AUC < 0.9 | 0.925 | 0.788 | 0.981 | 0.945 | 0.919 | 0.241 |
| AUC > 0.9 | 0.89 | 0.727 | 0.957 | 0.873 | 0.896 | 0.241 |
| Random 10 | 0.899 | 0.742 | 0.963 | 0.891 | 0.902 | 0.241 |
| Random 12 | 0.877 | 0.696 | 0.956 | 0.873 | 0.879 | 0.241 |
| Random 15 | 0.864 | 0.658 | 0.967 | 0.909 | 0.850 | 0.241 |
| Random 20 | 0.908 | 0.766 | 0.963 | 0.891 | 0.913 | 0.241 |
| Minimum | 0.842 | 0.623 | 0.949 | 0.836 | 0.832 | 0.241 |
| Maximum | 0.961 | 0.96 | 0.981 | 0.945 | 0.988 | 0.241 |
| Average | 0.917 | 0.810 | 0.960 | 0.880 | 0.930 | 0.241 |
| Standard Dev | 0.030 | 0.088 | 0.007 | 0.023 | 0.041 | N/A |

Models "10-21" are models using the 10-21 biomarkers within the 33 subset. The "Random 10, 12, 15, and 20" were additional random selections of 10, 12, 15, and 20 biomarkers, respectively, from the list of final biomarkers. The "AUC<0.8, <0.9, and >0.9" are models created of only biomarkers whose AUC was less than 0.8, 0.9 and greater than 0.9, respectively.

Conclusion

The Algorithm of this invention with 13 biomarkers has a sensitivity and specificity of 0.873 and 0.954. Algorithms with 33 biomarkers and 19 biomarkers both have a sensitivity of 0.891 and a specificity of 0.977. These algorithms will detect 87-89% of patients with NSCLC (or that 11-13 of 100 patients with NSCLC may not be detected). The specificity of these algorithms are at 0.954 and 0.977 meaning that 95-97% of patients who has the disease will be diagnosed as positive for NSCLC (or that 5 or 3 of 100 patients without the disease may test positive for the disease). The ROC Curves for the 33, 19 and 13 biomarkers have an AUC of 0.963, 0.960 and 0.951, respectively. Algorithms with 33 biomarkers, 19 biomarkers and 13 biomarkers have great potential for clinical use. When other non-NSCLC cancers were removed from analysis, the specificity of algorithms with 33 biomarkers, 19 biomarkers and 13 biomarkers improved to 0.991 or 99.1%. The sensitivity was not affected. The AUC for algorithms with 33 biomarkers, 19 biomarkers and 13 biomarkers improved to 0.974, 0.970 and 0.964, respectively.

Discussion

In the clinical setting, the PPV and NPV are more useful in determining the value of a test since these measures are indicative of the prevalence of the disease in the population of interest. The models in this study used samples that originated from the US. A highly sensitive is important where the test is used to identify a serious but treatable disease; and a high specific test avoids further subjection of the patient to further unnecessary follow-up medical procedures. In the case of lung cancer, LDCT methods have a high sensitivity but low specificity. A possible route is to subject patients who are initially positive to a test with high sensitivity/low specificity (LDCT), to a second test with low (or high) sensitivity/high specificity. This approach allows for nearly all of the false positives to be correctly identified as disease free.

As a primary diagnostic test, physicians may prefer a test with a much higher sensitivity and sacrifice specificity. The argument is that not detecting "a" cancer is more detrimental than a false negative. A combination of algorithms, high sensitivity/mid specificity or mid sensitivity/specificity, is an option for the CPC test and will be explored. Providing clinicians a continuous variable result with cut-off limitations is an alternative to a qualitative single score classifier of either a "Positive" or "Negative" for the presence of early stage non-small cell lung cancer.

The biomarkers and subsets of biomarkers selected using the Algorithm show an unexpected improvement in the early diagnosis of NSCLC.

The equations, formulas and relations contained in this disclosure are illustrative and representative and are not meant to be limiting. Alternate equations may be used to represent the same phenomena described by any given equation disclosed herein. In particular, the equations disclosed herein may be modified by adding error-correction terms, higher-order terms, or otherwise accounting for inaccuracies, using different names for constants or variables, or using different expressions. Other modifications, substitutions, replacements, or alterations of the equations may be performed.

All publications, patents, and published patent applications mentioned in this specification are herein incorporated by reference, in their entirety, to the same extent as if each individual publication, patent, or published patent application was specifically and individually indicated to be incorporated by reference.

The invention claimed is:

1. A method for assaying a plurality of biomarkers, wherein the method comprises
    obtaining a physiological sample from a subject; and
    measuring in the physiological sample a set of biomarkers, wherein the set of biomarkers comprises (i) NSE, CXCL9, CEA, CYFRA-21-1, and (ii) at least 9 biomarkers selected from the group consisting of IL-8, MMP-9, sTNFRII, TNFRI, MMP-7, IL-5, Resistin, IL-10, MPO, MCP-1, GRO-Pan, leptin, MIF, sICAM-1, IL-2, SAA, and PDFG-AB/BB, to produce test data comprising a plurality of biomarker measures.

2. The method of claim 1, wherein each biomarker is a peptide, protein, peptides and proteins bearing post-translational modifications, or a combination thereof.

3. The method of claim 2, wherein the physiological sample is a biological fluid.

4. The method of claim 3, wherein the biological fluid is blood, serum, plasma, or a mixture thereof.

5. The method of claim 1, wherein the biomarker measures are measured by immunoassay.

6. The method of claim 1, wherein the subject is 45 years old or older, is a long-term smoker, has been diagnosed with indeterminate nodules in the lungs, or a combination thereof.

7. The method of claim 1, wherein the set of biomarkers contains no more than 50 biomarkers.

8. The method of claim 1, wherein the set of biomarkers contains no more than 35 biomarkers.

9. A method for assaying a plurality of biomarkers, wherein the method comprises obtaining a physiological sample from a subject; and measuring in the physiological sample a set of biomarkers, wherein the set of biomarkers comprises (i) NSE, CXCL9, CEA, CYFRA-21-1, and either sTNFRII or PDFG-AB/BB, and (ii) at least 7 biomarkers selected from the group consisting of IL-8, MMP-9, TNFRI, MMP-7, IL-5, Resistin, IL-10, MPO, MCP-1, GRO-Pan, leptin, MIF, sICAM-1, IL-2, and SAA, to produce test data comprising a plurality of biomarker measures.

10. A method for assaying a plurality of biomarkers, wherein the method comprises obtaining a physiological sample from a subject; and measuring in the physiological sample a set of biomarkers, wherein the set of biomarkers comprises (i) NSE, CXCL9, CEA, CYFRA-21-1, sTNFRII, PDFG-AB/BB, and (ii) at least 7 biomarkers selected from the group consisting of IL-8, MMP-9, TNFRI, MMP-7, IL-5, Resistin, IL-10, MPO, MCP-1, GRO-Pan, leptin, MIF, sICAM-1, IL-2, and SAA, to produce test data comprising a plurality of biomarker measures.

\* \* \* \* \*